(12) United States Patent
Shrivastava

(10) Patent No.: US 8,871,765 B2
(45) Date of Patent: Oct. 28, 2014

(54) SUBSTITUTED 4-(4-FLUORO-3-(PIPERA-ZINE-1-CARBONYL)BENZYL)PHTHA-LAZIN-1(2H)-ONE DERIVATIVES AS POLY (ADP-RIBOSE) POLYMERASE-1 INHIBITORS

(75) Inventor: Brijesh Kumar Shrivastava, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 13/812,246

(22) PCT Filed: Jul. 7, 2011

(86) PCT No.: PCT/IN2011/000455
§ 371 (c)(1),
(2), (4) Date: Feb. 8, 2013

(87) PCT Pub. No.: WO2012/014221
PCT Pub. Date: Feb. 2, 2012

(65) Prior Publication Data
US 2013/0137695 A1    May 30, 2013

(30) Foreign Application Priority Data
Jul. 27, 2010 (IN) .......................... 2142/MUM/2010

(51) Int. Cl.
*A61K 31/502* (2006.01)
*C07D 237/32* (2006.01)
*C07D 401/12* (2006.01)

(52) U.S. Cl.
CPC ............ *C07D 237/32* (2013.01); *C07D 401/12* (2013.01)
USPC ...... 514/252.02; 544/239; 544/387; 546/148; 546/268.1

(58) Field of Classification Search
CPC ............................ A61K 31/502; C07D 237/32
USPC .............. 514/252.02; 544/239, 387; 546/148, 546/268.1
See application file for complete search history.

(56) References Cited

FOREIGN PATENT DOCUMENTS

WO    WO 2004/080976    9/2004

OTHER PUBLICATIONS

K.A. Menear et al., "4[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1," Journal of Medicinal Chemistry, vol. 51, 2008, pp. 6581-6591.
K.A. Menear et al., "Novel alkoxybenzamide inhibitors of poly(ADP-ribose) polymerase," Bioorganic & Medicinal Chemistry Letters, Pergamon, Elsevier Science, vol. 18, No. 14, Jul. 15, 2008, pp. 3942-3945.
International Search Report mailed Nov. 9, 2011.
K.A. Menear et al., "443-(4-Cyclopropanecarbonylpiperazine-1-carbony1)-4-fluorobenzyl]- 2H-phthalazin-l-on: A Novel Bioavailable Inhibitor of Poly(ADP-ribose) Polymerase-l", Journal of Medicinal Chemistry, vol. 51, 2008, pp. 6581-6591.
K.A. Menear et al., "Novel Alkoxybenzamide Inhibitors of Poly (ADP-ribose) Polymerase", Bioorganic & Medicinal Chemistry Letters, Pergamon, Elsevier Science, vol. 18, No. 14, Jul. 15, 2008, pp. 3942-3945.

*Primary Examiner* — Douglas M Willis
(74) *Attorney, Agent, or Firm* — Nixon & Vanderhye P.C.

(57) ABSTRACT

Disclosed are compounds of general formula (I), their stereoisomers, regioisomers, tautomeric forms and novel intermediates involved in their synthesis, their pharmaceutically acceptable salts. These compounds are suitable as Poly(ADP-ribose)polymerase-1 inhibitors (PARP-1 inhibitors).

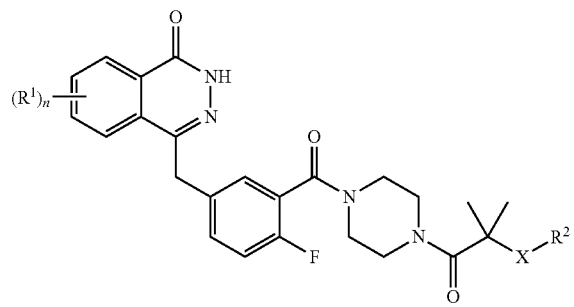

12 Claims, No Drawings

SUBSTITUTED 4-(4-FLUORO-3-(PIPERAZINE-1-CARBONYL)BENZYL)PHTHALAZIN-1(2H)-ONE DERIVATIVES AS POLY (ADP-RIBOSE) POLYMERASE-1 INHIBITORS

This application is the U.S. national phase of International Application No. PCT/IN2011/000455 filed 7 Jul. 2011 which designated the U.S. and claims priority to IN 2142/MUM/2010 filed 27 Jul. 2010, the entire contents of each of which are hereby incorporated by reference.

FIELD OF THE INVENTION

The present invention relates to novel compounds of general formula (I), their stereoisomers, regioisomers, tautomeric forms and novel intermediates involved in their synthesis, their pharmaceutically acceptable salts, pharmaceutically acceptable solvates and pharmaceutical compositions containing them. The present invention also relates to a process of preparing novel compounds of general formula (I), their stereoisomers, regioisomers, their tautomeric forms, their pharmaceutically acceptable salts, pharmaceutically acceptable solvates, pharmaceutical compositions containing them, and novel intermediates involved in their synthesis.

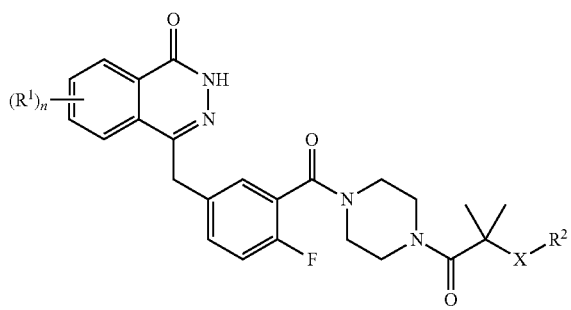

(I)

The present invention is further directed to compounds, which cause selective inhibition of the poly(ADP-ribose) polymerase-1.

BACKGROUND AND PRIOR ART

Exploitation of synthetic lethal relationship is a trustworthy therapeutic strategy, to target genetic differences between tumor and normal cells which eventually provide large therapeutic window for the treatment of cancer. Poly(ADP-ribose) polymerase-1 (PARP-1, 113 kDa) is a prototype member of the 17 member PARP protein superfamily. PARP-1 is a nuclear protein whose zinc finger DNA binding domain localizes PARP-1 to the site of DNA damage. This NAD dependent enzyme catalyzes poly(ADP-ribosylation) of proteins, involved in the detection and repair of DNA damage. It plays a frontal role in the decision of a cell to live or to die in a stress situation [Senthil kumar B., Rajmohan, et al., *Mol. Cell. Biol.* 2009, 29 (15), 4116-4129]. The primary structure of the enzyme is highly conserved in eukaryotes with human enzyme having 92% homology with mouse enzyme at the level of amino acid sequence and a 50 amino acid block showing 100% homology between vertebrates [Virag Laszlo and Szabo Csaba, *Pharmacol. Reviews* 2002, 54 (3), 375-429]. Studies on the molecular mechanism of PARP-1 suggests that, it is involved in various DNA related functions including gene amplifications, cell division, differentiation, apoptosis, DNA base excision repair and also effects on telomere length and chromosome stability [d'Add di Fagogna et al., *Nature. Gen.* 1999, 23 (10), 76-80].

It has been reported that PARP-1 modulates DNA repair and other processes and can produce long chains of poly (ADP-ribose) within the cell nucleus which is central to its activity [Althaus, F. R.; Richter, C. *Mol. Biol., Biochem. Biophys.* 1987, 37, 1-237]. Different studies on knock out mouse models, report that the deletion of PARP-1 impairs DNA repair but is not embryonically lethal. Double knock out PARP-1 and PARP-2 mice die during early embryogenesis, which shows that PARP-2 as the closest homolog of PARP-1 (62% identical in its catalytic domain to PARP-1) & plays a major role in the DNA repair during the absence of PARP-1 enzyme [Ratnam Kapil and Law Jenifer A. *Clin. Cancer Res.* 2007, 17 (5), 1383-1388]. A group of scientists from Newcastle University and University of Konstanz, in *British Journal of Cancer* 2009, 101 (2), 256-26, claims to be the first to directly compare PARP-1 polymorphisms, cellular levels of PARP-1 protein and PARP activity in a systematic way and reveals that PARP activity depends on other factors beside the level of protein and the active site SNP.

In a recent review from *Free Radical Biology & Medicine* 2009, 47, 13-26 suggests that PARP inhibitors could be used not only as chemo/radiotherapy sensitizers, but also as single agents to selectively kill cancers which are due to defect in DNA repair, specifically cancers with mutations in the breast cancer-associated gene (BRCA1 and BRCA2). PARP becomes activated in response to oxidative DNA damage and depletes cellular energy pools, thus leading to cellular dysfunction in various tissues. The activation of PARP may also induce various cell death processes and promotes an inflammatory response associated with multiple organ failure.

Recently some of the investigators have demonstrated in *Biochem. Pharmacol.* 2009, 77, 1348-1357 that PARP inhibitors combined with DNA-damage inducing cytostatic agents like taxol can lead to effective tumor therapy through activation of PI-3-kinase-Akt pathway.

The American Society of Clinical Oncology held its Annual Meeting in Orlando, Fla. (May 29-Jun. 2, 2009) reported in *Eur. J. Cancer* 2009, 45, 1897-1901 that two drugs Olaparib and BSI-201 from a new class of targeted agents called poly(ADP-ribose)polymerase (PARP) inhibitors have demonstrated significant activity against hard-to treat breast cancers, according to findings from two separate phase II trials.

Several small molecules that specifically target PARP-1 enzyme as an inhibitor are being investigated and among them BSI 201 (BiPar) is in Phase III clinical trial and AG 14699 (Cancer Res. UK), AZD 2281 (KuDOS), ABT 888 (Abbott) are in Phase II clinical trial, with promising initial results. However, special attention must be paid to the possibility that enhanced therapeutic efficacy might be accompanied by increased off-target effects because of effect on DNA-repair mechanism in normal tissues.

Recent findings have thrust poly(ADP-ribose)polymerases (PARPs) into the limelight as potential chemotherapeutic targets as described in *Nature Reviews Cancer* 4 Mar. 2010, 1-9. Crystal Structure of the Catalytic Domain of Human PARP2 in Complex with PARP Inhibitor ABT-888 reported by [Herwig Schuler et al., *Pharmacol. Biochemistry* 2010, 49, 1056-1058]

Novel compounds which are selective PARP-1 inhibitors, their preparation and their use in medicine have also been reported in WO 2002036576, WO 2006039545, WO 2007062413, WO 2004080976, WO 2009093032, WO 2008047082, WO 2001042219, WO 2005066163, WO 2006106326, WO 2008146035, WO 2006021801, US 20090192156, which are incorporated as references in their entirety.

Synthesis of pthalazinone derivatives of the following general formula and having the potential to inhibit PARP for the treatment of cancer or for potentiating tumor cells for the treatment with ionizing radiation or chemotherapeutic agents has been disclosed in US 2009/0192156 A1 and WO 2009/093032 A1.

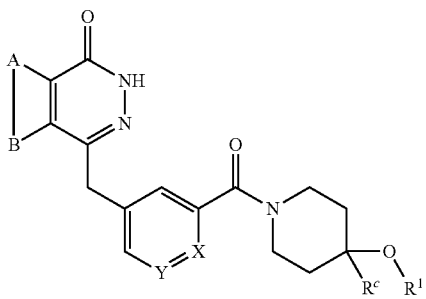

Synthesis of thiophene carboxamide class of compounds as the combination of CHK and PARP inhibitors for the treatment of cancer is disclosed in WO 2008146035 A1 and WO 2005066163 A2. Representative compounds have the following general formula.

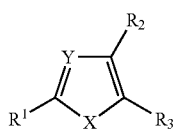

X is selected from NH, S and O. Y is selected from CH or N.

Crystalline form and improved method for the synthesis of particular pthalazinone derivatives and use of the crystalline form as PARP-1 Inhibitor has been reported in WO 2008047082. Representative compounds have the following structure:

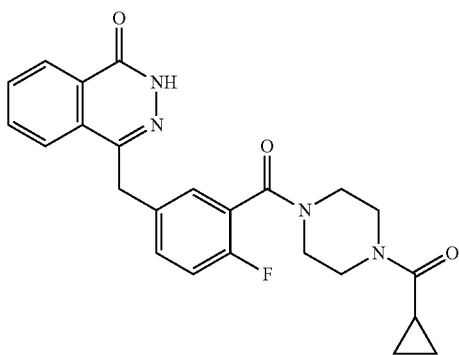 [SMILES: O=C(c1cc(Cc2n[nH]c(=O)c3ccccc23)ccc1F)N1CCN(C(=O)C2CC2)CC1]

Synthesis of 4-heteroarylmethyl substituted pthalazinone derivatives has been disclosed in WO 2006021801 A1 and WO 2004080976 A1 for use in treating cancer or other diseases ameliorated by the inhibition of PARP.

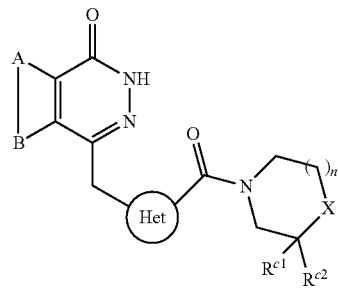

wherein, A and B together represent an optionally substituted, fused aromatic ring; X can be $NR^X$ or $CR^XR^Y$; If $X=NR^X$ then n is 1 or 2 and if $X=CR^XR^Y$ then n is 1; $R^X$ is selected from the group consisting of H, optionally substituted $C_{1-20}$ alkyl, $C_{1-20}$ aryl, $C_{(3-20)}$ heterocyclyl, thioamido, ester, acyl, and sulfonyl groups; $R^Y$ is selected from H, hydroxyl, amino; $R^X$ and $R^Y$ may together form a Spiro $C_{3-7}$ cycloalkyl or heterocyclyl group; $R^{C1}$ and $R^{C2}$ are independently selected from the group consisting of H and $C_{1-4}$ alkyl; $R^1$ is selected from H and halo; And Het is selected from

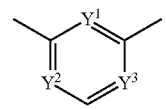

where $Y^1$ is selected from CH and N, $Y^2$ is selected from CH and N, $Y^3$ is selected from CH, CF and N, where one or two of $Y^1$, $Y^2$, and $Y^3$ can be N; and

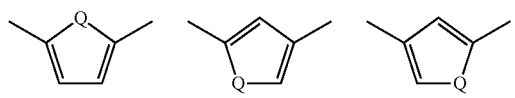

where Q is O or S.

Optimization of Phenyl-Substituted Benzimidazole Carboxamide Poly(ADP-Ribose)5-Benzamidoisoquinolin-1-ones and 5-(ω-Carboxyalkyl)isoquinolin-1-ones as Isoform-Selective Inhibitors of Poly(ADP-ribose) Polymerase 2 (PARP-2) has been described in *J. Med. Chem.* 2011, 54, 2049-2059 by Peter T. Sunderland et. al.

Tumor Growth Inhibition by Olaparib in BRCA2 Germline-Mutated Patient-Derived Ovarian Cancer Tissue Xenografts has been recently published in *Clin Cancer Res* 2011, 17, 783-791.

Simultaneous determination of ABT-888, a poly(ADP-ribose)polymerase inhibitor, and its metabolite in human plasma by liquid chromatography/tandem mass spectrometry has been described in *Journal of Chromatography B,* 2011, 878, 333-339.

'Polymerase Inhibitors: Identification of (S)-2-(2-Fluoro-4-(pyrrolidin-2-yl)phenyl)-1H-benzimidazole-4-carboxamide (A-966492), a highly Potent and Efficacious Inhibitor' has been described in *J. Med. Chem.,* 2010, 53, 3142-3153.

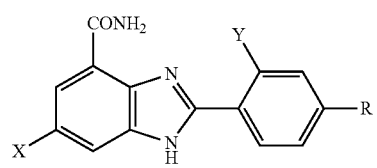

Design, synthesis of Quinoline-8-carboxamides, a new class of Poly(adenosine-diphosphate-ribose)polymerase-1

(PARP-1) Inhibitor has been described in *J. Med. Chem.* 2009, 52, 868-877. Synthesis of 2-[(R)-2-methylpyrrolidin-2-yl]-1H-benzimidazole-4-carboxamide as a Poly(ADP-ribose) Polymerase (PARP) Inhibitor has been disclosed in *J. Med. Chem.* 2009, 52, 514-523.

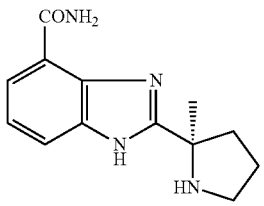 [SMILES: C[C@]1(c2nc3c(C(N)=O)cccc3[nH]2)CCCN1]

Synthesis of aminoethyl pyrrolo dihydroisoquinolinones as novel poly(ADP-ribose) polymerase-1 inhibitors has been described in *Bioorg. Med. Chem. Lett.* 2009, 19, 4042-4045. Representative compounds have the following general formula.

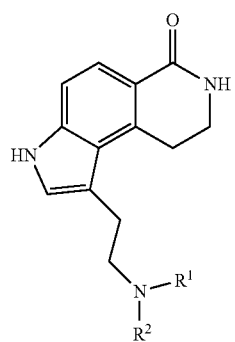

Synthesis of isoquinolinone-based tetracycles as poly (ADP-ribose) polymerase-1 (PARP-1) inhibitors inhibitors has been described in *Bioorg. Med. Chem. Lett.* 2009, 19, 7537-7541. Representative compounds have the following general formula.

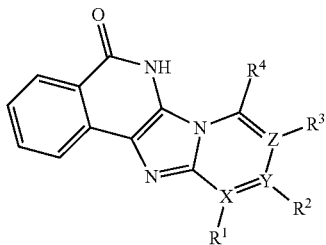

Identification of substituted pyrazolo[1,5-a]quinazolin-5 (4H)-one as potent poly(ADP-ribose)polymerase-1 (PARP-1) inhibitors has been described in *Bioorg. Med. Chem. Lett.* 2009, 19, 4196-4200. Representative compounds have the following general formula

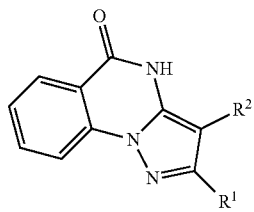

Synthesis of novel tricyclic quinoxalinone as the inhibitors of poly(ADP-ribose) polymerase-1 (PARP-1) has been stated in *Bioorg. Med. Chem. Lett.* 2009, 19, 4050-4054. Representative compounds have the following general formula.

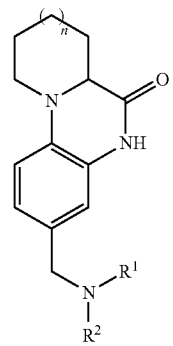

Identification of ring-fused pyrazolo pyridin-2-ones as novel poly(ADP-ribose) polymerase-1 inhibitors has been published in *Bioorg. Med. Chem. Lett.* 2008, 18, 5126-5129. This describes compounds of the following general formula.

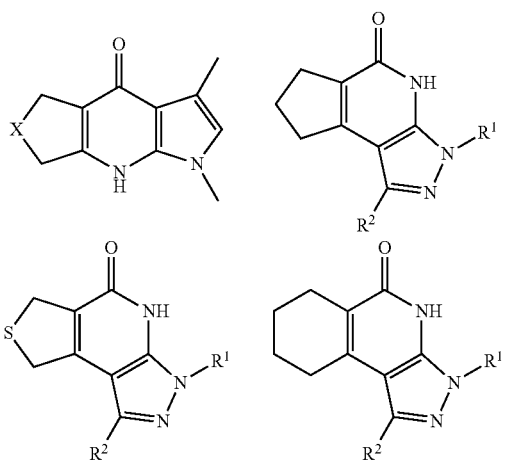

Discovery of Orally Active and Brain-Penetrable Quinoxalinone Inhibitors of Poly(ADP-ribose)polymerase has been disclosed in *J. Med. Chem.* 2004, 47, 4151-4154 and describes compounds of the following general formula.

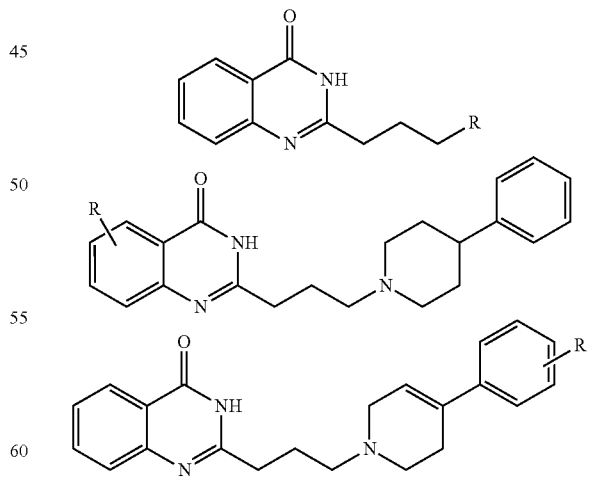

Discovery of potent Poly(ADP-ribose) Polymerase-1 Inhibitors from the modification of Indeno[1,2-c]isoquinolinone and the described compounds of the following general formula I has been reported in *J. Med. Chem.* 2005, 48, 5100-5103.

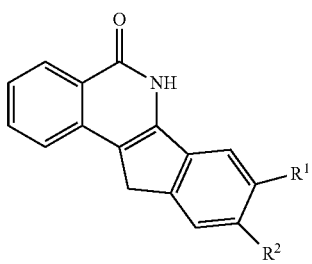

(1)

Though several compounds have been reported in the literature as PARP-1 inhibitors, very few have actually shown actual clinical benefits and none have been approved so far. Looking at the large unmet medical needs, there appears a need for developing further compounds which have better safety and efficacy profile. We herein disclose a new series of compounds which shows potential as PARP-1 inhibitors.

SUMMARY OF THE INVENTION

The present invention describes novel compounds useful as poly(ADP-ribose) polymerase-1 inhibitors. The compounds are defined by the general formula (I) below:

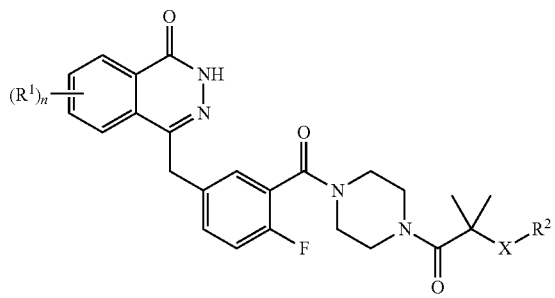

(I)

The compounds of the present invention acts by inhibiting PARP1 enzyme to prevent the process of DNA repair and induce cell mediated apoptosis. As a result of compromised repair, PARP-1 deficient or inhibited cells are more sensitive to DNA damaging agents (γ radiation, topoisomerase inhibitors, and alkylating agents). The compounds of the present invention are selective inhibitors of the poly(ADP-ribose) polymerase-1.

OBJECTS OF THE INVENTION

The main objective of the present invention is to provide novel compounds of general formula (I), their stereoisomers, tautomeric forms, their regioisomers, novel intermediates involved in their synthesis, their pharmaceutically acceptable salts, their pharmaceutically acceptable solvates and pharmaceutical compositions containing them or their mixtures and their use in medicine.

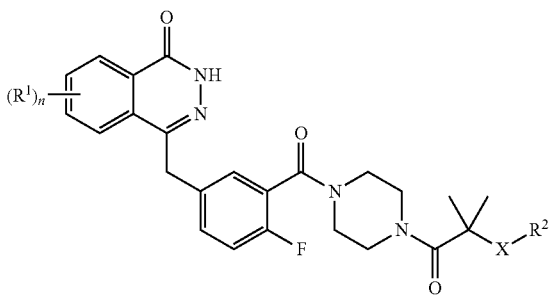

(I)

In an embodiment of the present invention is provided a process for the preparation of novel compounds of general formula (I), their stereoisomers, regioisomers and their tautomeric forms, novel intermediates involved in their synthesis, pharmaceutically acceptable salts, pharmaceutically acceptable solvates and pharmaceutical compositions containing them.

In a further embodiment is provided a method of treatment of diseases which can be treated or whose symptoms can be reversed with by administering a therapeutically effective & non-toxic amount of the compound of formula (I) or their pharmaceutically acceptable compositions to the mammals.

DETAILED DESCRIPTION OF THE INVENTION

The compounds of the present invention are defined by the general formula (I) below:

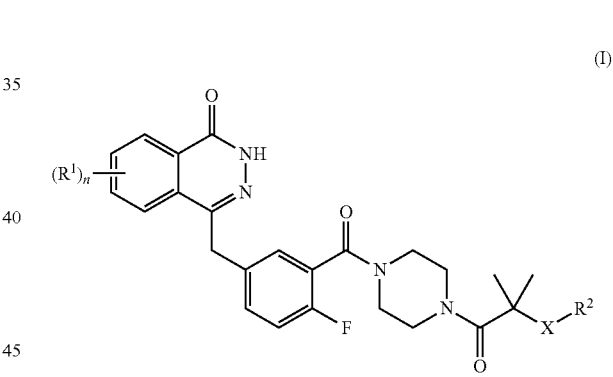

(I)

wherein $R^1$ at each occurrence is independently selected from H, halogen, nitro, nitrile, or the groups selected from ($C_1$-$C_{12}$) alkyl, haloalkyl, cycloalkyl, alkylthio or the group ($OSO_2$) alkyl, wherein each of these groups may be further substituted by suitable substituents selected from those disclosed hereinafter below;

n=1-3;

'X' may be selected from —O, —S, $SO_2$, SO, —NH;

$R^2$ is selected from aryl, heteroaryl or heteroaromatic groups wherein each of these groups may be substituted further with suitable substituents selected from those described below;

Suitable substituents wherever applicable includes, but are not limited to the following radicals, alone or in combination with other radicals, hydroxyl, oxo, halo, thio, nitro, amino, alkyl, alkoxy, haloalkyl or haloalkoxy groups.

In a preferred embodiment, the groups representing the above may be selected from those described hereinafter.

The "aryl" groups may be selected from phenyl, naphthyl, tetrahydronaphthyl, indenyl, dihydroindenyl, biphenyl groups and each of these groups may be optionally substituted with one or more substituents selected from hydrogen, halogen, alkyl, alkoxy, hydroxyl, haloalkyl, haloalkoxy, cyano, thioalkyl, cycloalkyl groups;

The "heteroaryl" or "heteroaromatic" group is selected from suitable single or fused mono, bi or tricyclic aromatic heterocyclic radicals containing one or more hetero atoms selected from O, N or S, more preferably the groups are selected from pyridyl, thienyl, furyl, pyrrolyl, indolinyl, indolyl, pyridofuranyl, pyridothienyl, thienopyrimidyl, quinolinyl, pyrimidinyl, pyrazolyl, quinazolinyl, pyridazinyl, purinyl groups, each of these groups may be further optionally substituted with one or more substituents selected from hydrogen, halogen, alkyl, alkoxy, hydroxyl, haloalkyl, haloalkoxy, aryl, aralkyl, cyano, alkylthio, thioalkyl groups;

the "heterocyclyl" group may be selected from suitable saturated, partially saturated or unsaturated aromatic or non aromatic mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thienopiperidinyl, groups, each of these groups may be optionally substituted with one or more substituents selected from hydrogen, halogen, alkyl, alkoxy, hydroxyl, haloalkyl, haloalkoxy, aryl, aralkyl, cyano, alkylthio, thioalkyl groups;

In a further embodiment the groups, radicals described above may be selected from:

the "alkyl" group used either alone or in combination with other radicals, denotes a linear or branched radical containing one to six carbons, selected from methyl, ethyl, n-propyl, iso-propyl, n-butyl, sec-butyl, tent-butyl, amyl, t-amyl, n-pentyl, n-hexyl, and the like;

the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "haloalkyl" group is selected from an alkyl radical, as defined above, suitably substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio;

the group "aralkyl" represents an aryl group as defined above attached to an alkyl group as described above;

the group "heteroaralkyl" and "heterocyclyclakyl" represents heteroaryl and heterocyclyl groups respectively as defined above attached to an alkyl group as defined above.

The compounds of formula (I) may optionally be converted to their suitable pharmaceutically acceptable salts by processes as are known in the art. The novel compounds of the present invention can further be formulated into suitable pharmaceutically acceptable compositions by combining with suitable excipients by techniques and processes and concentrations as are well known.

The compounds of the present invention modulate PARP-1 receptor and are useful as a therapeutic target for many diseases and especially for the treatment of cancer.

The compounds prepared according to present invention include, but are not limited to:

4-(4-fluoro-3-(4-(2-methyl-2-((5-(trifluoromethyl)pyridin-2-yl)oxy)propanoyl)piperazine-1-carbonyl)benzyl)phthalazin-1(2H)-one;

4-(4-fluoro-3-(4-(2-methyl-2-(4-nitrophenoxy)propanoyl)perazine-1-carbonyl)benzyl)phthalazin-1(2H)-one;

4-(4-fluoro-3-(4-(2-methyl-2-(4-methoxy)phenoxy)propanoyl)piperazine-1-carbonyl)benzyl)phthalazin-1(2H)-one;

4-(4-fluoro-3-(4-(2-methyl-2-(4-chlorophenoxy)propanoyl)piperazine-1-carbonyl)benzyl)phthalazin-1(2H)-one;

4-(4-fluoro-3-(4-(2-methyl-2-(4-fluorophenoxy)propanoyl)piperazine-1-carbonyl)benzyl)phthalazin-1(2H)-one;

4-(4-fluoro-3-(4-(2-methyl-2-phenoxypropanoyl)piperazine-1-carbonyl)benzyl)phthalazin-1(2H)-one;

4-(3-(4-(2-((4-chlorophenyl)thio)-2-methylpropanoyl)piperazine-1-carbonyl)-4-fluorobenzyl)phthalazin-1(2H)-one 4-(4-fluoro-3-(4-(2-methyl-2-(p-tolyloxy)propanoyl)piperazine-1-carbonyl)benzyl)phthalazin-1(2H)-one;

4-(4-fluoro-3-(4-(2-(3-methoxyphenoxy)-2-methylpropanoyl)piperazine-1-carbonyl)benzyl)phthalazin-1(2H)-one;

4-(4-fluoro-3-(4-(2-methyl-2-(naphthalen-2-yloxy)propanoyl)piperazine-1-carbonyl)benzyl)phthalazin-1(2H)-one;

4-(3-(4-(2-((2-chlorophenyl)thio)-2-methylpropanoyl)piperazine-1-carbonyl)-4-fluorobenzyl)phthalazin-1(2H)-one;

4-(3-(4-(2-((4-chloronaphthalen-1-yl)oxy)-2-methylpropanoyl)piperazine-1-carbonyl)-4-fluorobenzyl)phthalazin-1(2H)-one;

4-(4-fluoro-3-(4-(2-((2-fluorophenyl)amino)propanoyl)piperazine-1-carbonyl)benzyl)phthalazin-1(2H)-one;

4-(4-fluoro-3-(4-(2-(isoquinolin-5-yloxy)-2-methyl-propanoyl)piperazine-1-carbonyl)benzyl)phthalazin-1(2H)-one;

4-(3-(4-(2-(2,5-dimethylphenoxy)-2-methylpropanoyl)piperazine-1-carbonyl)-4-fluorobenzyl)phthalazin-1(2H)-one;

4-(3-(4-(2-(2,3-dichlorophenoxy)-2-methylpropanoyl)piperazine-1-carbonyl)-4-fluorobenzyl)phthalazin-1(2H)-one;

4-(4-fluoro-3-(4-(2-methyl-2-(pyridin-2-yloxy)propanoyl)piperazine-1-carbonyl)benzyl)phthalazin-1(2H)-one;

6-bromo-4-(3-(4-(2-(cyclopentylthio)-2-methylpropanoyl)piperazine-1-carbonyl)-4-fluorobenzyl)phthalazin-1(2H)—)-one;

4-(4-fluoro-3-(4-(2-methyl-2-(2-nitrophenoxy)propanoyl)piperazine-1-carbonyl)benzyl)phthalazin-1(2H)-one;

4-(3-(4-(2-(4-bromo-2-chlorophenoxy)-2-methylpropanoyl) piperazine-1-carbonyl)-4-fluorobenzyl)phthalazin-1(2H)-one;

4-(4-fluoro-3-(4-(2-methyl-2-(3-(trifluoromethyl)phenoxy) propanoyl)piperazine-1-carbonyl)benzyl)phthalazin-1 (2H)-one;

4-(4-fluoro-3-(4-(2-((4-fluorophenyl)thio)-2-methylpropanoyl)piperazine-1-carbonyl)benzyl)phthalazin-1(2H)-one;

4-(4-fluoro-3-(4-(2-methyl-2-(phenylsulfonyl)propanoyl) piperazine-1-carbonyl)benzyl)phthalazin-1(2H)-one;

4-(4-fluoro-3-(4-(2-((4-fluorophenyl)sulfonyl)-2-methylpropanoyl)piperazine-1-carbonyl)benzyl)phthalazin-1 (2H)-one;

4-(4-fluoro-3-(4-(2-((4-fluorophenyl)sulfonyl)-2-methylpropanoyl)piperazine-1-carbonyl)benzyl)phthalazin-1 (2H)-one;

4-(3-(4-(2-(2,4-difluorophenoxy)-2-methylpropanoyl)piperazine-1-carbonyl)-4-fluorobenzyl)phthalazin-1(2H)-one;

4-(3-(4-(2-((2,4-difluorophenyl)thio)-2-methylpropanoyl) piperazine-1-carbonyl)-4-fluorobenzyl)phthalazin-1(2H)-one;

4-(4-fluoro-3-(4-(2-((3-methoxyphenyl)thio)-2-methylpropanoyl)piperazine-1-carbonyl)benzyl)phthalazin-1(2H)-one;

4-(3-(4-(2-((2-bromophenyl)thio)-2-methylpropanoyl)piperazine-1-carbonyl)-4-fluorobenzyl)phthalazin-1(2H)-one;

4-(3-(4-(2-((3,4-dichlorophenyl)thio)-2-methylpropanoyl) piperazine-1-carbonyl)-4-fluorobenzyl)phthalazin-1(2H)-one;

4-(3-(4-(2-((2,4-dichlorophenyl)thio)-2-methylpropanoyl) piperazine-1-carbonyl)-4-fluorobenzyl)phthalazin-1(2H)-one;

4-(4-fluoro-3-(4-(2-((3-fluorophenyl)thio)-2-methylpropanoyl)piperazine-1-carbonyl)benzyl)phthalazin-1(2H)-one;

4-(3-(4-(2-((2,5-dichlorophenyl)thio)-2-methylpropanoyl) piperazine-1-carbonyl)-4-fluorobenzyl)phthalazin-1(2H)-one;

4-(4-fluoro-3-(4-(2-((4-fluorophenyl)amino)-2-methylpropanoyl)piperazine-1-carbonyl)-benzyl)phthalazin-1(2H)-one;

4-(4-fluoro-3-(4-(2-methyl-2-(phenylamino)-propanoyl) piperazine-1-carbonyl)benzyl)phthalazin-1(2H)-one;

4-(3-(4-(2-(cyclopentylthio)-2-methylpropanoyl)piperazine-1-carbonyl)-4-fluorobenzyl)phthalazin-1(2H)-one;

4-(3-(4-(2-(4-bromo-3,5-dimethylphenoxy)-2-methylpropanoyl)piperazine-1-carbonyl)-4-fluorobenzyl)phthalazin-1(2H)-one;

4-(4-fluoro-3-(4-(2-methyl-2-(pyridin-2-ylthio)propanoyl) piperazine-1-carbonyl)benzyl)phthalazin-1(2H)-one;

4-(3-(4-(2-(2,4-dichlorophenylsulfinyl)-2-methylpropanoyl) piperazine-1-carbonyl)-4-fluorobenzyl)phthalazin-1(2H)-one;

4-(3-(4-(2-((3-bromophenyl)sulfonyl)-2-methylpropanoyl) piperazine-1-carbonyl)-4-fluorobenzyl)phthalazin-1(2H)-one;

4-(4-fluoro-3-(4-(2-((2-fluorophenyl)thio)-2-methylpropanoyl)piperazine-1-carbonyl)benzyl)phthalazin-1(2H)-one;

4-(3-(4-(2-((3-bromophenyl)thio)-2-methylpropanoyl)piperazine-1-carbonyl)-4-fluorobenzyl)phthalazin-1(2H)-one;

4-(3-(4-(2-((3-chlorophenyl)thio)-2-methylpropanoyl)piperazine-1-carbonyl)-4-fluorobenzyl)phthalazin-1(2H)-one;

6-bromo-4-(4-fluoro-3-(4-(2-methyl-2-(pyridin-2-ylthio) propanoyl)piperazine-1-carbonyl)benzyl)phthalazin-1 (2H)-one;

4-(4-fluoro-3-(4-(2-methyl-2-((2-nitropyridin-3-yl)oxy)propanoyl)piperazine-1-carbonyl)benzyl)phthalazin-1(2H)-one;

4-(4-fluoro-3-(4-(2-methyl-2-(phenylthio)propanoyl)piperazine-1-carbonyl)benzyl)phthalazin-1(2H)-one;

4-(3-(4-(2-((4-bromophenyl)thio)-2-methylpropanoyl)piperazine-1-carbonyl)-4-fluorobenzyl)phthalazin-1(2H)-one;

4-(4-fluoro-3-(4-(2-methyl-2-(2,3,5,6-tetrafluorophenoxy) propanoyl)piperazine-1-carbonyl)benzyl)phthalazin-1 (2H)-one;

4-(3-(4-(2-((2,5-dimethylphenyl)thio)-2-methylpropanoyl) piperazine-1-carbonyl)-4-fluorobenzyl)phthalazin-1(2H)-one;

4-(3-(4-(2-((2,4-dimethylphenyl)thio)-2-methylpropanoyl) piperazine-1-carbonyl)-4-fluorobenzyl)phthalazin-1(2H)-one;

Suitable groups and substituents on the groups may be selected from those described anywhere in the specification.

The compounds of the present invention may be prepared using the methods described below, together with conventional techniques known to those skilled in the art of organic synthesis, or variations thereon as appreciated by those skilled in the art. Referred methods include, but are not limited to those described below, where all symbols are as defined earlier.

The compounds of the present invention can be prepared according to the following schemes $1^a$, $2^a$ and $3^a$.

Synthesis of Compound of General Formula (I)

General Process of Preparation:

Compounds of general formula (II) can be synthesized from compounds of general formula (III) by hydrolysis with NaOH. Compounds of general formula (III) can be synthesized from the compounds of the general formula (II) by reacting it with ethyl 2-bromo-2-methylpropanoate in the presence of suitable bases such as $Cs_2CO_3$, $K_2CO_3$ in ACN, DMF & the like or their suitable mixtures.

Compounds of the general formula (V) can be synthesized by processes reported in *J. Med. Chem.* 2008, 51, 6581-6591 with suitable modifications/alterations as required which are within the skills of a skilled person.

Compounds of the general formula (I) can be synthesized by coupling the compounds of the general formula (V) with the compounds of the general formula (II), using suitable coupling agents such as TBTU, DMAP, DCC, HOBt.$H_2O$, and EDC. HCl, & the like in the presence of organic bases such as DIPEA, TEA, pyridine, & the like in the solvents such as tetrahydrofuran, dimethyl formamide, dichloromethane, chloroform & the like or their suitable mixtures at ambient temperature.

Compounds of general formula (IV) can be synthesized from compounds of general formula (I) by oxidized by using suitable reagents such as Oxone, MCPBA, $H_2O_2$ and the like in the solvents such as methanol, tetrahydrofuran, toluene, dichloromethane, chloroform, acetic acid & the like or their suitable mixtures.

Scheme 1[a]:

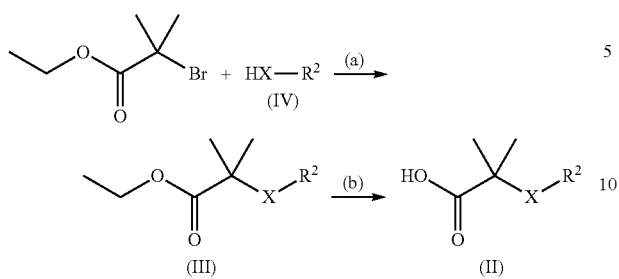

[a]Reagents and Conditions: (a) Cs₂CO₃, ACN, 65-70° C., 14 h; (b) NaOH, ACN, water, 75-80° C., 3 h;

Scheme 2[a]:

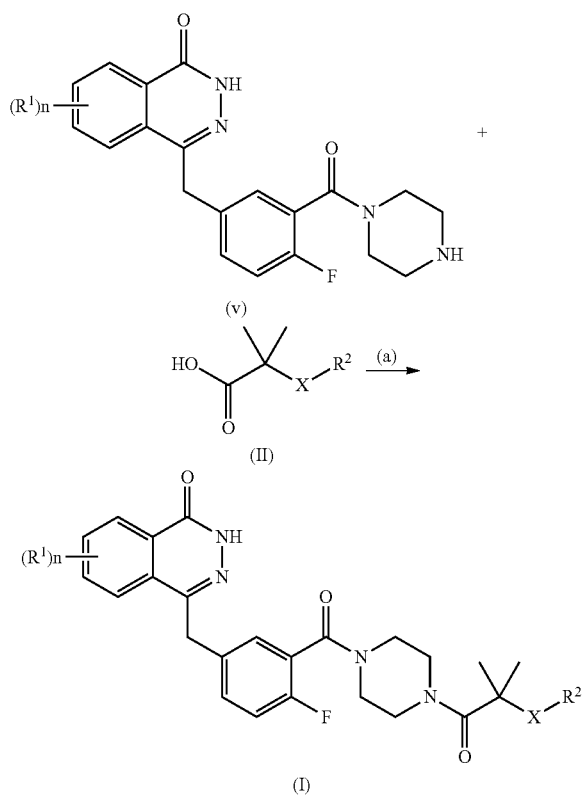

[a]Reagents and Conditions: (a) TBTU, DIPEA, DMF, 25-27° C., 2 h

Scheme 3[a]:

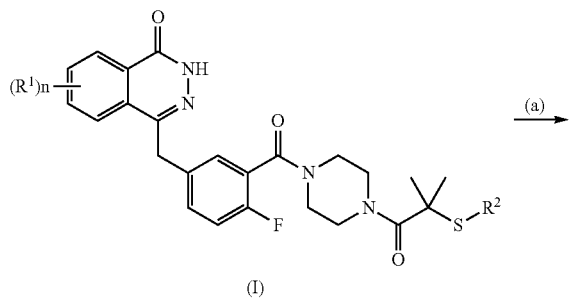

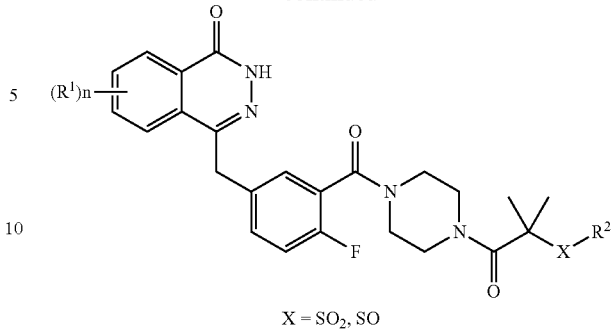

[a]Reagents and Conditions: (a) Oxone, MeOH, H₂O, 0-30° C., 12 h

The invention is further exemplified by the following non-limiting examples which are provided for exemplifying the invention and should not be construed as limiting the scope of the invention in any ways. It will be appreciated that the other embodiments which are not exemplified can be easily practiced by a skilled person using his routine skills after reading the specific examples provided below. Such changes/alterations/modifications etc. which may be required to practice the full scope of the invention as described and claimed in the present invention are well within the scope of a person skilled in the art.

Unless otherwise specified, 1H NMR spectral data given in the examples are recorded using a 400 MHz spectrometer (Bruker Topspin 2.0) and reported in δ scale. Tetramethyl silane is used as the internal standard.

Example 1

Synthesis of 4-(4-fluoro-3-(4-(2-methyl-2-((5-(trifluoromethyl)pyridin-2-yl)oxy)propanoyl)piperazine-1-carbonyl)benzyl)phthalazin-1(2H)-one Step 1: Preparation of ethyl 2-methyl-2-((5-(trifluoromethyl)pyridin-2-yl)oxy)propanoate.

To 5-(trifluoromethyl)pyridin-2-ol (2.5 g, 15 mmol) in ACN (25 mL), Cesium carbonate (9.98 g, 30 mmol) followed by ethyl 2-bromo-2-methylpropanoate (2.27 mL, 15 mmol) was added and the reaction mixture was heated at 65-70° C. for 14 h. The progress of reaction was checked by TLC using mobile phase 50% ethyl acetate in pet ether. The reaction mixture was cooled to 30-35° C., solvents were evaporated on a rotatory evaporator under reduced pressure to afford the semisolid brown compound. The suspension was diluted with water and then extracted with ethyl acetate. The organic layer was washed with water, dried over anhydrous Na₂SO₄ and solvents were evaporated on a rotatory evaporator under reduced pressure to afford tert-butyl 2-((4-oxo-3,4-dihydrophthalazin-1-yl) methyl)-6,7-dihydrothieno[3,2-c]pyridine-5 (4H)-carboxylate as liquid compound (1.4 g, 32%).

Step 2: Preparation of ethyl 2-methyl-2-((5-(trifluoromethyl)pyridin-2-yl)oxy)propanoic acid.

To a solution of NaOH (0.40 g, 10 mmol) in ACN (10 mL) and water (10 mL) was added tert-butyl 2-((4-oxo-3,4-dihydrophthalazin-1-yl)methyl)-6,7-dihydrothieno[3,2-c]pyridine-5 (4H)-carboxylate (1.4 g, 5 mmol) at room temperature. The above mixture was stirred at 75-80° C. for 3 h. The progress of reaction was checked by TLC using mobile phase 20% ethyl acetate in pet ether. The resulting mixture was transferred into single neck R.B. flask and solvents were evaporated on a rotatory evaporator under reduced pressure, cooled to 0-5° C., and acidify using dil. HCl solution to pH=4. The suspension was then extracted with ethyl acetate. The organic layer was washed with water, dried over anhydrous $Na_2SO_4$ and solvents were evaporated on a rotatory evaporator under reduced pressure to afford ethyl 2-methyl-2-((5-(trifluoromethyl)pyridin-2-yl)oxy)propanoic acid as off-white solid (0.8 g, 63%).

Step 3: Preparation of 4-(4-fluoro-3-(4-(2-methyl-2-((5-(trifluoromethyl) pyridin-2-yl)oxy)propanoyl)piperazine-1-carbonyl)benzyl)phthalazin-1(2H)-one.

To a solution of 2-methyl-2-((5-(trifluoromethyl)pyridin-2-yl)oxy)propanoic acid (0.204 g, 0.81 mmol) in dry DMF (6 mL) was added TBTU (0.289 g, 0.90 mmol) at room temperature under atmosphere of nitrogen. To this 4-(4-fluoro-3-(piperazine-1-carbonyl)benzyl)phthalazin-1(2H)-one (0.3 g, 0.81 mmol) and DIPEA (0.303 mL, 1.74 mmol) were added. The reaction mixture was stirred at room temperature for 2 h. The progress of reaction was checked by TLC by using mobile phase 5% methanol in chloroform. The reaction mixture was diluted with ethyl acetate. The organic layer was washed with water, dried over anhydrous $Na_2SO_4$ and solvents were evaporated on a rotatory evaporator under reduced pressure to crude solid which was purified by the flash column chromatography using eluent chloroform:methanol (98.3:1.7) to afford 4-(4-fluoro-3-(4-(2-methyl-2-((5-(trifluoromethyl)pyridin-2-yl)oxy)propanoyl)piperazine-1-carbonyl)benzyl)phthalazin-1(2H)-one as white solid (0.230 g, 47%).

$^1$H-NMR (400 MHz, DMSO-$d_6$) δ 12.57 (s, 1H), 8.49 (s, 1H), 8.24 (d, J=8.8 Hz, 1H), 8.09 (d, J=7.2 Hz, 1H), 7.92 (d, J=7.2 Hz, 1H), 7.86-7.80 (m, 2H), 7.40-7.37 (m, 1H), 7.28 (d, J=4.8 Hz, 1H), 7.22-7.15 (m, 2H), 7.00 (s, 1H), 4.31-4.25 (m, 2H), 3.55 (t, J=14.8 Hz, 2H), 3.38-3.25 (m, 2H), 2.73 (s, 1H), 1.61 (s, 6H).

Following compounds (Example 2 to Example 38 and Example 41 to Example 50) are prepared following the process described in scheme $1^a$, scheme $2^a$ and as further exemplified in example 1, by using appropriate starting materials and suitable modifications including suitable variation and/or alteration which is well within the scope of a person skilled in the art.

Example 2

4-(4-fluoro-3-(4-(2-methyl-2-(4-nitrophenoxy)propanoyl)piperazine-1-carbonyl)benzyl)phthalazin-1(2H)-one $^1$H-NMR 12.56 (s, 1H), 8.19-8.25 (brt, 3H), 7.80-7.84 (brt, 2H), 7.39 (brs, 1H), 7.27 (brs, 1H), 7.18 (brs, 1H), 4.28 (s, 2H), 3.72 (brs, 1H), 3.55 (brs, 3H), 3.07 (brs, 3H), 2.87 (brs, 1H), 1.60-1.62 (brd, 6H).

Example 3

4-(4-fluoro-3-(4-(2-methyl-2-(4-methoxyphenoxy)propanoyl)piperazine-1-carbonyl)benzyl)phthalazin-1(2H)-one $^1$H-NMR δ 12.57 (s, 1H), 8.24 (d, J=7.6 Hz, 1H), 7.93 (brs, 1H), 7.81 (brs, 2H), 7.93 (brs, 1H), 7.32 (brs, 1H), 7.19 (brs, 1H), 6.82-6.84 (brd, 2H), 6.74 (brs, 2H), 4.29 (s, 2H), 3.89 (brs, 1H), 3.67 (brs, 1H), 3.63 (brs, 3H), 3.57-3.60 (brt, 2H), 3.44 (brs, 2H), 3.12 (brs, 1H), 2.92 (brs, 1H), 1.46 (s, 6H).

Example 4

4-(4-fluoro-3-(4-(2-methyl-2-(4-chlorophenoxy)propanoyl)piperazine-1-carbonyl)benzyl)phthalazin-1(2H)-one $^1$H-NMR δ 12.56 (s, 1H), 8.24 (t, J=4.6 Hz, 1H), 7.92 (brs, 1H), 7.79-7.83 (brt, 2H), 7.40-7.41 (brd, 1H), 7.31 (brs, 3H), 7.19-7.21 (brd, 1H), 6.79 (brs, 2H), 4.29 (s, 2H), 3.80 (brs, 1H), 3.64 (brs, 1H), 3.43-3.55 (brd, 3H), 3.10 (brs, 2H), 2.86 (brs, 1H), 1.51-1.53 (s, 6H).

Example 5

4-(4-fluoro-3-(4-(2-methyl-2-(4-fluorophenoxy)propanoyl)piperazine-1-carbonyl)benzyl)phthalazin-1(2H)-one $^1$H-NMR δ 12.56 (s, 1H), 8.24 (d, J=7.2 Hz, 1H), 7.92 (s, 1H), 7.81-7.82 (brd, 2H), 7.40 (brs, 1H), 7.31 (brs, 1H), 7.17-7.21 (brt, 1H), 7.11 (brs, 2H), 6.80 (brs, 1H), 4.47 (brs, 2H), 3.44 (brs, 1H), 3.11 (brs, 1H), 2.88 (brs, 1H), 1.50 (brs, 6H).

Example 6

4-(4-fluoro-3-(4-(2-methyl-2-(pyridin-2-yloxy)propanoyl)piperazine-1-carbonyl)benzyl)phthalazin-1(2H)-one $^1$H-NMR δ 12.56 (s, 1H), 8.23-8.26 (t, J=4.4 Hz, 1H), 8.05-8.07 (m, 1H), 7.92 (d, J=7.6 Hz, 1H), 7.80-7.85 (m, 2H), 7.71 (s, 1H), 7.37-7.40 (m, 1H), 7.26 (s, 1H), 7.15-7.19 (t, J=8.6 Hz, 1H), 6.97-7.00 (t, J=6.0 Hz, 1H), 6.78 (s, 1H), 4.28 (s, 2H), 3.56-3.60 (m, 5H), 3.00 (s, 2H), 2.58 (s, 1H), 1.57 (s, 6H).

Example 7

4-(4-fluoro-3-(4-(2-methyl-2-phenoxypropanoyl)piperazine-1-carbonyl)benzyl)phthalazin-1(2H)-one $^1$H-NMR δ 12.56 (s, 1H), 8.23-8.25 (t, J=4.6 Hz, 1H), 7.81-7.93 (m, 3H), 7.19-7.39 (m, 5H), 6.96 (s, 1H), 6.78 (s, 2H), =4.8 Hz, 1H), 4.28 (s, 2H), 3.41-3.82 (m, 5H), 3.20 (s, 1H), 3.07 (s, 1H), 2.71 (s, 1H), 1.54 (s, 6H).

Example 8

4-(3-(4-(2-((4-chlorophenyl)thio)-2-methylpropanoyl)piperazine-1-carbonyl)-4-fluorobenzyl)phthalazin-1(2H)-one $^1$H-NMR δ 12.59 (s, 1H), 8.23-8.25 (m, 1H), 7.95 (d, J=8.0 Hz, 1H), 7.85-7.90 (m, 1H) 7.79-7.88 (m, 1H), 7.35-7.46 (m, 6H), 7.21-7.26 (m, 1H), 6.96 (s, 1H), 4.32 (s, 2H), 3.66-3.80 (m, 6H), 3.23 (s, 2H), 1.42 (s, 6H).

Example 9

4-(4-fluoro-3-(4-(2-methyl-2-(p-tolyloxy)propanoyl)piperazine-1-carbonyl)benzyl)phthalazin-1(2H)-one $^1$H-NMR δ 12.57 (s, 1H), 8.24 (d, J=8.0 Hz, 1H), 7.81-7.92 (m, 1H), 7.39 (s, 1H), 7.30 (s, 1H), 7.18 (s, 1H), 7.13-7.06 (m, 1H), 6.67 (s, 1H), 4.36 (s, 2H), 4.29 (s, 2H), 3.55-3.01 (m, 4H), 2.96 (s, 2H), 2.84 (s, 1H), 2.31 (s, 3H), 1.48 (s, 6H).

Example 10

4-(4-fluoro-3-(4-(2-(3-methoxyphenoxy)-2-methyl-propanoyl)piperazine-1-carbonyl)benzyl)phthalazin-1(2H)-one $^1$H-NMR δ 12.57 (s, 1H), 8.24 (t, J=4.6 Hz, 1H), 7.92-7.81 (m, 3H), 7.39 (s, 1H), 7.31 (s, 1H), 7.16 (d, J=6.8 Hz, 1H), 6.55 (d, J=8.8 Hz, 1H), 6.37-6.33 (m, 2H), 4.29 (s, 2H), 3.81 (s, 1H), 3.68 (d, 4H), 3.58-3.43 (m, 3H), 3.07 (s, 1H), 2.82 (s, 1H), 1.53 (d, 6H), 0.83 (d, 1H).

Example 10

4-(4-fluoro-3-(4-(2-methyl-2-(naphthalen-2-yloxy)propanoyl)piperazine-1-carbonyl)benzyl)phthalazin-1(2H)-one $^1$H-NMR δ 12.55 (s, 1H), 8.23 (t, J=4.2 Hz, 1H), 7.82-7.91 (brt, 5H), 7.72 (t, J=8 Hz, 1H), 7.44 (t, J=7.4 Hz, 1H), 7.37 (t, J=7.2 Hz, 2H), 7.26 (brs, 1H), 7.07-7.11 (brt, 3H), 4.25 (brs, 2H), 3.70-3.85 (brd, 2H), 2.79 (brs, 1H), 1.60-1.62 (brd, 6H)

Example 11

4-(3-(4-(2-((2-chlorophenyl)thio)-2-methylpropanoyl)piperazine-1-carbonyl)-4-fluorobenzyl)phthalazin-1(2H)-one $^1$H-NMR δ 12.58 (s, 1H), 8.25 (t, J=7.6 Hz, 1H), 7.95 (d, J=8 Hz, 1H), 7.85-7.89 (m, 1H), 7.81 (t, J=7.2 Hz, 1H), 7.54 (dd, J=8 & 2 Hz, 1H), 7.41-7.45 (m, 2H), 7.30-7.37 (m, 3H), 7.22 (t, J=9 Hz, 1H), 4.31 (s, 2H), 3.80 (brs, 2H), 3.55-3.80 (m, 4H), 3.19 (brs, 2H), 1.47 (s, 6H)

Example 12

4-(3-(4-(2-((4-chloronaphthalen-1-yl)oxy)-2-methylpropanoyl)piperazine-1-carbonyl)-4-fluorobenzyl)phthalazin-1(2H)-one $^1$H-NMR δ 12.55 (s, 1H), 8.23-8.31 (brt, 2H), 8.11 (brs, 1H), 7.82-7.94 (brq, 2H), 7.61-7.73 (m, 3H), 7.57 (d, J=8.4 Hz, 1H), 7.10-7.38 (m, 3H), 6.68 (d, J=8.4 Hz, 1H), 7.10-7.38 (m, 3H), 6.68 (t, J=8.4 Hz, 1H), 4.21-4.28 (brd, 2H), 3.55-3.79 (m, 4H), 3.46 (brs, 1H), 3.10 (brs, 2H), 2.87 (s, 1H), 1.65-1.69 (brd, 6H)

Example 13

4-(4-fluoro-3-(4-(2-((2-fluorophenyl)amino)propanoyl)piperazine-1-carbonyl)benzyl)phthalazin-1(2H)-one $^1$H-NMR δ 12.57 (s, 1H), 8.25 (d, J=7.6 Hz, 1H), 7.95 (d, J=8 Hz, 1H), 7.88 (dd, 7.6 & 1.6 Hz, 1H), 7.82 (dd, J=15.6 & 7.6 Hz, 1H), 7.43 (brs, 1H), 7.34-7.36 (brd, 1H), 7.20-7.24 (brt, 1H), 6.95 (brs, 1H), 5.20 (brd, 1H), 4.51-4.46 (s, 2H), 3.58-3.76 (m, 4H), 3.45-3.53 (brt, 2H), 3.21 (brs, 2H), 1.21-1.28 (brq, 3H)

Example 14

4-(4-fluoro-3-(4-(2-(isoquinolin-5-yloxy)-2-methyl-propanoyl)piperazine-1-carbonyl)benzyl)phthalazin-1(2H)-one $^1$H-NMR δ 12.56 (bs, 1H), 8.22-8.30 (m, 1H), 7.76-7.92 (m, 5H), 7.35-7.39 (m, 2H), 7.21-7.25 (m, 1H), 7.11-7.19 (m, 2H), 6.93-6.95 (m, 1H), 6.71-6.76 (m, 1H), 4.24-4.29 (m, 2H), 3.80-3.81 (m, 1H), 3.65-3.66 (m, 1H), 3.49-3.59 (m, 2H), 3.37-3.43 (m, 2H), 3.31-3.37 (m, 2H), 1.79 (s, 6H)

Example 15

4-(3-(4-(2-(2,5-dimethylphenoxy)-2-methylpropanoyl)piperazine-1-carbonyl)-4-fluorobenzyl)phthalazin-1(2H)-one $^1$H-NMR δ 12.56 (s, 1H), 8.24 (t, J=7.2 Hz, 1H), 7.92-7.81 (m, 3H), 7.41 (d, J=5.6 Hz, 1H), 7.29 (d, J=8.4 Hz, 1H), 7.19 (m, 1H), 7.06-7.01 (m, 1H), 6.67 (d, J=6.8 Hz, 1H), 6.44 (m, 1H), 4.28 (s, 2H), 3.79 (s, 1H), 3.63-3.55 (m, 2H), 3.45 (m, 2H), 3.28-3.05 (m, 2H), 2.76 (bs, 1H), 2.17 (s, 3H), 2.12-2.02 (d, 3H), 1.53 (d, 6H)

Example 16

4-(3-(4-(2-(2,3-dichlorophenoxy)-2-methylpropanoyl)piperazine-1-carbonyl)-4-fluorobenzyl)phthalazin-1(2H)-one $^1$H-NMR δ 12.56 (s, 1H), 8.24 (t, J=7.2 Hz, 1H), 7.92-7.81 (m, 3H), 7.40 (bs, 1H), 7.32-7.28 (m, 3H), 7.19 (m, 1H) 6.82-6.80 (dd, J=6.8 & 3.2 Hz, 1H), 4.29 (s, 2H), 3.79 (s, 1H), 3.63-3.58 (m, 3H), 3.44 (m, 2H), 3.10 (s, 1H), 2.9 (s, 1H), 1.58 (d, 6H)

Example 17

4-(4-fluoro-3-(4-(2-methyl-2-(pyridin-2-yloxy) propanoyl) piperazine-1-carbonyl)benzyl)phthalazin-1(2H)-one $^1$H-NMR δ 12.56 (s, 1H), 8.23-8.26 (t, J=4.4 Hz, 1H), 8.05-8.07 (m, 1H), 7.92 (d, J=7.6 Hz, 1H), 7.80-7.85 (m, 2H), 7.71 (s, 1H), 7.37-7.40 (m, 1H), 7.26 (s, 1H), 7.15-7.19 (t, J=8.6 Hz, 1H), 6.97-7.00 (t, J=6.0 Hz, 1H), 6.78 (s, 1H), 4.28 (s, 2H), 3.56-3.60 (m, 5H), 3.00 (s, 2H), 2.58 (s, 1H), 1.57 (s, 6H).

Example 18

6-bromo-4-(3-(4-(2-((3-chlorophenyl)thio)-2-methylpropanoyl)piperazine-1-carbonyl)-4-fluorobenzyl)phthalazin-1(2H)-one $^1$H-NMR δ 12.57 12.71 (s, 1H), 8.16 (d, J=8.4 Hz, 2H), 7.46-7.38 (m, 5H), 7.34 (dd, J=2.8 Hz and 1.2 Hz, 1H), 7.25 (t, 1H), 4.34 (s, 2H), 3.9 (s, 2H), 3.67 (s, 4H), 3.28 (d, 2H), 1.45 (s, 6H)

Example 19

4-(4-fluoro-3-(4-(2-methyl-2-(2-nitrophenoxy)propanoyl)piperazine-1-carbonyl)benzyl)phthalazin-1(2H)-one $^1$H-NMR δ 12.56 (s, 1H), 8.24 (d, J=6.8 Hz, 1H), 7.94 (s, 1H), 7.86-7.81 (m, 3H), 7.60 (dd, J=8.4 Hz and 1.2 Hz, 1H), 7.40 (dd, J=8.2 Hz and 6 Hz, 1H), 7.30 (s, 1H) 7.18 (dd, J=15.6 Hz and 1.6 Hz, 2H), 6.95 (d, J=9.6 Hz, 1H), 4.29 (s, 2H), 3.82 (s, 2H), 3.59 (m, 3H), 3.09 (s, 1H), 2.85 (s, 1H), 2.85 (s, 1H), 1.57 (d, 6H)

Example 20

4-(3-(4-(2-(4-bromo-2-chlorophenoxy)-2-methylpropanoyl)piperazine-1-carbonyl)-4-fluorobenzyl)phthalazin-1(2H)-one $^1$H-NMR δ 12.57 (s, 1H), 8.24 (d, J=6.8 Hz, 1H), 7.73-7.92 (brq, 4H), 7.46 (dd, J=8.8, 2.4 Hz, 1H), 7.40-7.42 (brt, 1H), 7.32 (brs, 1H), 6.77 (d, J=8.8 Hz, 1H), 4.29 (s, 2H), 3.79 (brs, 1H), 3.55-3.61 (m, 3H), 3.44 (brs, 1H), 3.11 (brs, 1H), 2.92 (brs, 1H), 1.55-156 (brd, 6H)

Example 21

4-(4-fluoro-3-(4-(2-methyl-2-(3-(trifluoromethyl)phenoxy)propanoyl)piperazine-1-carbonyl)benzyl)phthalazin-1(2H)-one $^1$H-NMR δ 12.57 (s, 1H), 8.23 (brt, 1H), 7.92 (brs, 1H), 7.82 (d, J=7.2 Hz, 2H), 7.52 (brs, 1H), 7.39 (brs, 1H), 7.30-7.39 (brt, 2H), 7.19 (brs, 1H), 7.06-7.08 (brd, 2H), 4.28 (brs, 2H), 3.41-3.63 (brq, 5H), 3.20 (brs, 1H), 3.06 (brs, 1H), 2.80 (brs, 1H), 1.55-158 (brd, 6H)

Example 22

4-(4-fluoro-3-(4-(2-((4-fluorophenyl)thio)-2-methylpropanoyl)piperazine-1-carbonyl)benzyl)phthalazin-1(2H)-one $^1$H-NMR δ 12.59 (s, 1H), 7.24 (dd, J=7.6 & 0.8 Hz, 1H), 7.95 (d, J=8 Hz, 1H), 7.85-7.90 (m, 1H), 7.79-7.83 (m, 1H), 7.41-7.46 (m, 3H), 7.18-7.26 (m, 3H), 4.33 (s, 2H), 3.68-3.80 (brd, 6H), 3.25 (s, 2H), 1.40 (s, 6H)

Example 23

4-(4-fluoro-3-(4-(2-methyl-2-(phenylsulfonyl)propanoyl)piperazine-1-carbonyl)benzyl)phthalazin-1(2H)-one $^1$H-NMR δ 12.60 (s, 1H), 8.25 (d, J=1.2 Hz, 1H), 7.97 (d, J=8 Hz, 1H), 7.88-7.92 (m, 1H), 7.75-7.85 (m, 4H), 7.64 (t, J=7.8 Hz, 2H), 7.43-7.47 (m, 1H), 7.39 (dd, J=6.4 & 2 Hz, 2H),), 7.25 (t, J=9 Hz, 1H), 4.34 (brs, 2H), 3.58-3.73 (m, 6H), 3.27-3.28 (brd, 2H), 1.56 (s, 6H)

Example 24

4-(4-fluoro-3-(4-(2-((4-fluorophenyl)sulfonyl)-2-methylpropanoyl)piperazine-1-carbonyl)benzyl)phthalazin-1(2H)-one $^1$H-NMR δ 12.60 (s, 1H), 8.25 (dd, J=8 & 1.2 Hz, 1H), 7.96 (d, J=7.6 Hz, 1H), 7.86-7.91 (m, 3H), 7.80-7.84 (m, 1H), 7.43-7.50 (m, 3H), 7.36 (dd, J=6.4 & 2 Hz, 2H),), 7.24 (t, J=9 Hz, 1H), 4.33 (brs, 2H), 3.49-3.68 (brd, 6H), 3.25 (brs, 2H), 1.56 (s, 6H)

Example 25

4-(4-fluoro-3-(4-(2-((4-fluorophenyl)sulfinyl)-2-methylpropanoyl)piperazine-1-carbonyl)benzyl)phthalazin-1(2H)-one $^1$H-NMR δ 12.60 (s, 1H), 8.26 (dd, J=7.6 & 0.8 Hz, 1H), 7.96 (d, J=7.6 Hz, 1H), 7.90 (dd, J=7.6 & 1.6 Hz, 1H), 7.86 (dd, J=7.6 & 0.8 Hz, 1H), 7.65-7.68 (m, 21-1), 7.35-7.47 (m, 4H), 7.24 (t, J=9 Hz, 1H), 4.33 (brs, 2H), 3.50-3.64 (brt, 6H), 3.20 (brs, 2H), 1.50 (s, 3H), 1.13 (s, 3H)

Example 26

4-(3-(4-(2-(2,4-difluorophenoxy)-2-methylpropanoyl)piperazine-1-carbonyl)-4-fluorobenzyl)phthalazin-1(2H)-one $^1$H-NMR δ 12.59 (s, 1H), 8.25 (d, J=7.2 Hz, 1H), 7.95 (d, J=6.4 Hz, 1H), 7.82 (brs, 2H), 7.44 (d, J=5.6 Hz, 1H), 7.34 (t, J=9 Hz, 2H), 6.92-7.04 (m, 2H), 4.31 (brs, 2H), 3.77-3.92 (brd, 2H), 3.57-3.61 (brq, 4H), 3.07-3.17 (brd, 2H), 1.50 (s, 6H)

Example 27

4-(3-(4-(2-((2,4-difluorophenyl)thio)-2-methylpropanoyl)piperazine-1-carbonyl)-4-fluorobenzyl)phthalazin-1(2H)-one $^1$H-NMR δ 12.60 (s, 1H), 8.25-8.27 (m, 1H), 7.97 (d, J=7.6 Hz, 1H), 7.87-7.91 (m, 1H), 7.81-7.84 (m, 1H), 7.51-7.55 (m, 1H), 7.43-7.46 (m, 1H), 7.35-7.40 (m, 1H), 7.25 (t, J=9 Hz, 2H), 7.11-7.16 (m, 1H), 4.34 (s, 2H), 3.69-3.79 (brd, 6H), 3.27 (brs, 2H), 1.41 (s, 6H)

Example 28

4-(4-fluoro-3-(4-(2-((3-methoxyphenyl)thio)-2-methylpropanoyl)piperazine-1-carbonyl)benzyl)phthalazin-1(2H)-one $^1$H-NMR δ 12.59 (s, 1H), 8.26 (dd, J=8 & 1.2 Hz, 1H), 7.97 (d, J=7.6 Hz, 1H), 7.86-7.91 (m, 1H), 7.82-7.84 (brt, 1H), 7.42-7.45 (m, 1H), 7.39 (dd, J=6.4 & 2 Hz, 1H), 7.22-7.29 (m, 2H), 6.95 (dd, J=8.8 & 2.4 Hz, 2H), 6.89 (t, J=2 Hz, 1H), 4.33 (s, 2H), 3.32-3.42 (brd, 4H), 3.78-4.33 (brs, 2H), 3.73 (s, 3H), 3.66 (brs, 4H), 3.24 (brs, 2H), 1.44 (s, 6H)

Example 29

4-(3-(4-(2-((2-bromophenyl)thio)-2-methylpropanoyl)piperazine-1-carbonyl)-4-fluorobenzyl)phthalazin-1(2H)-one $^1$H-NMR δ 12.59 (s, 1H), 8.26 (dd, J=7.6 & 0.8 Hz, 1H), 7.96 (d, J=7.6 Hz, 1H), 7.86-7.90 (m, 1H), 7.80-7.84 (m, 1H), 7.71 (dd, J=7.6 & 0.4 Hz, 1H), 7.41-7.45 (m, 1H), 7.35-7.39 (m, 3H), 7.21-7.27 (m, 2H), 4.33 (s, 2H), 3.57-3.75 (m, 6H), 3.18 (s, 2H), 1.50 (s, 6H)

Example 30

4-(3-(4-(2-((3,4-dichlorophenyl)thio)-2-methylpropanoyl)piperazine-1-carbonyl)-4-fluorobenzyl)phthalazin-1(2H)-one $^1$H-NMR δ 12.59 (s, 1H), 8.26 (dd, J=7.6 & 0.8 Hz, 1H), 7.95 (d, J=7.6 Hz, 1H), 7.87-7.91 (m, 1H), 7.82-7.84 (brt, 1H), 7.64 (d, J=8 Hz, 1H), 7.61 (d, J=2 Hz, 1H), 7.41-7.52 (m, 1H), 7.33-7.38 (m, 2H), 7.25 (t, J=9 Hz, 1H), 4.33 (s, 2H), 3.67-3.82 (brd, 6H), 3.24 (brs, 2H), 1.46 (s, 6H)

Example 31

4-(3-(4-(2-((2,4-dichlorophenyl)thio)-2-methylpropanoyl)piperazine-1-carbonyl)-4-fluorobenzyl)phthalazin-1(2H)-one $^1$H-NMR δ 12.59 (s, 1H), 8.27 (dd, J=8 & 1.2 Hz, 1H), 7.96 (d, J=7.6 Hz, 1H), 7.84-7.90 (m, 2H), 7.75 (d, J=2 Hz, 1H), 7.41-7.46 (m, 3H), 7.37 (dd, J=6.4 & 2 Hz, 1H), 7.24 (t, J=9 Hz, 1H), 4.33 (s, 3.64-3.75 (brd, 6H), 3.21 (brs, 2H), 1.48 (s, 6H)

Example 32

4-(4-fluoro-3-(4-(2-((3-fluorophenyl)thio)-2-methylpropanoyl)piperazine-1-carbonyl)benzyl)phthalazin-1(2H)-one $^1$H-NMR δ 12.59 (s, 1H), 7.26 (dd, J=7.6 & 0.8 Hz, 1H), 7.97 (d, J=7.6 Hz, 1H), 7.80-7.91 (m, 2H), 7.37-7.46 (m, 3H), 7.17-7.26 (m, 4H), 4.33 (s, 2H), 3.66-3.83 (brt, 6H), 3.23 (s, 2H), 1.46 (s, 6H)

Example 33

4-(3-(4-(2-((2,5-dichlorophenyl)thio)-2-methylpropanoyl)piperazine-1-carbonyl)-4-fluorobenzyl)phthalazin-1(2H)-one $^1$H-NMR δ 12.59 (s, 1H), 8.26 (dd, J=7.6 & 0.8 Hz, 1H), 7.96 (d, J=7.6 Hz, 1H), 7.80-7.90 (m, 2H), 7.58 (t, J=4.2 Hz, 1H), 7.42-7.46 (m, 3H), 7.38 (dd, J=6.4 & 2.4 Hz, 1H), 7.23 (t, J=9 Hz, 1H), 4.32 (s, 2H), 3.61-3.82 (brt, 6H), 3.19 (brs, 2H), 1.52 (s, 6H)

Example 34

4-(4-fluoro-3-(4-(2-((4-fluorophenyl)amino)-2-methylpropanoyl)piperazine-1-carbonyl)-benzyl)phthalazin-1(2H)-one $^1$H-NMR δ 12.56 (bs, 1H), 8.24-8.31 (m, 1H), 7.81-7.93 (m, 3H), 7.31-7.40 (m, 3H), 7.17-7.21 (m, 1H), 6.89-6.93 (m, 2H), 6.45 (m, 2H), 5.80-5.93 (m, 1H), 4.29-4.33 (m, 2H), 3.83-3.98 (m, 2H), 3.75-3.79 (m, 2H), 2.67-2.79 (m, 2H), 1.40 (s, 6H)

Example 35

4-(4-fluoro-3-(4-(2-methyl-2-(phenylamino)-propanoyl)piperazine-1-carbonyl)benzyl)phthalazin-1(2H)-one $^1$H-NMR δ 12.55 (bs, 1H), 8.24-8.26 (d, J=9.2 Hz, 1H), 7.91 (m, 1H), 7.82-7.84 (m, 2H), 7.38-7.39 (m, 1H), 7.27-7.30 (dd, J=6.4 & 2.4 Hz, 1H), 7.17-7.20 (d, J=9.2 Hz, 1H), 7.02-7.06 (m, 2H), 6.52-6.55 (m, 1H), 6.45-6.47 (m, 2H), 5.80-5.90 (m, 1H), 4.28-4.32 (m, 2H), 3.90-4.00 (m, 1H), 3.60-3.70 (m, 1H), 3.30-3.40 (m, 1H), 2.90-3.00 (m, 1H), 1.44 (s, 6H)

Example 36

4-(3-(4-(2-(cyclopentylthio)-2-methylpropanoyl)piperazine-1-carbonyl)-4-fluorobenzyl)phthalazin-1(2H)-one $^1$H-NMR δ 12.58 (s, 1H), 8.26 (d, J=7.6 Hz, 1H), 7.96 (d, J=8.0 Hz, 1H), 7.91-7.87 (dd, J=7.6 Hz & 1.2 Hz, 1H), 7.82 (t, J=7.6 Hz, 1H), 7.45-7.42 (m, 1H), 7.38-7.36 (dd, J=6.4 Hz & 2.0 Hz, 1H), 7.23 (t, J=9.2 Hz, 1H), 4.33 (s, 2H), 3.75 (br s, 2H), 3.62 (br s, 4H), 3.20 (br s, 2H), 3.02-2.97 (m, 1H), 1.96-1.90 (m, 2H), 1.65-1.53 (m, 2H), 1.50-1.44 (m, 8H), 1.41-1.29 (m, 2H)

Example 37

4-(3-(4-(2-(4-bromo-3,5-dimethylphenoxy)-2-methylpropanoyl)piperazine-1-carbonyl)-4-fluorobenzyl)phthalazin-1(2H)-one $^1$H-NMR δ 12.57 (s, 1H), 8.24 (d, J=1.2 Hz, 1H), 7.82-7.94 (brq, 3H), 7.41 (s, 1H), 7.33 (d, J=4.4 Hz, 1H), 7.20 (s, 1H), 6.63-6.68 (brt, 2H), 4.30 (s, 2H), 3.46-3.82 (m, 6H), 2.91-3.10 (brd, 2H), 3.31 (s, 6H), 1.52 (s, 6H)

Example 38

4-(4-fluoro-3-(4-(2-methyl-2-(pyridin-2-ylthio)propanoyl)piperazine-1-carbonyl)benzyl)phthalazin-1(2H)-one $^1$H-NMR δ 12.57 (s, 1H), 8.40 (d, J=3.6 Hz, 1H), 8.26 (dd, J=7.6 & 1.2 Hz, 1H), 7.93-7.95 (brt, 1H), 7.82-7.87 (m, 3H), 7.67-7.71 (m, 4H), 7.40-7.42 (m, 1H), 7.27-7.29 (m, 2H), 7.17-7.23 (m, 2H), 4.31 (s, 2H), 3.50-3.90 (brt, 6H), 3.05-3.07 (brt, 2H), 1.58 (s, 6H)

Example 39

4-(3-(4-(2-(2,4-dichlorophenylsulfinyl)-2-methylpropanoyl)piperazine-1-carbonyl)-4-fluorobenzyl)phthalazin-1(2H)-one To 4-(3-(4-(2-((2,4-dichlorophenyl)thio)-2-methylpropanoyl)piperazine-1-carbonyl)-4-fluorobenzyl)phthalazin-1(2H)-one (2.5 g, 15 mmol) in MeOH (25 mL) was added dropwise a solution of Oxone (9.98 g, 30 mmol) in water (25 mL) at 0° C. after addition reaction mixture stirred at 0° C. for 4 h. The progress of reaction was checked by TLC using mobile phase 50% ethyl acetate in pet ether. The reaction mixture was evaporated on a rotatory evaporator under reduced pressure to afford the semisolid off-white compound. The suspension was diluted with water and then extracted with ethyl acetate. The organic layer was washed with brine solution, dried over anhydrous Na2SO4 and solvents were evaporated on a rotatory evaporator under reduced pressure to afford 4-(3-(4-(2-(2,4-dichlorophenyl)sulfinyl)-2-methylpropanoyl)piperazine-1-carbonyl)-4-fluorobenzyl)phthalazin-1(2H)-one (39) as off-white crystals compound (1.4 g, 32%)

$^1$H-NMR δ 12.58 (s, 1H), 8.25 (dd, J=7.6 & 1.2 Hz, 1H), 7.95 (d, J=7.6 Hz, 1H), 7.79-7.90 (m, 2H), 7.74 (d, J=1.6 Hz, 1H), 7.40-7.45 (m, 2H), 7.36 (dd, J=6.4 & 2 Hz, 1H), 7.23 (t, J=9 Hz, 1H), 4.33 (s, 2H), 3.63-3.79 (brd, 6H), 3.20 (s, 2H), 1.47 (s, 6H)

Example 40

4-(3-(4-(2-((3-bromophenyl)sulfonyl)-2-methylpropanoyl)piperazine-1-carbonyl)-4-fluorobenzyl)phthalazin-1(2H)-one To 4-(3-(4-(2-((2,4-dichlorophenyl)thio)-2-methylpropanoyl)piperazine-1-carbonyl)-4-fluorobenzyl)phthalazin-1(2H)-one (2.5 g, 15 mmol) in MeOH (25 mL) was added dropwise a solution of Oxone (9.98 g, 30 mmol) in water (25 mL) at 0° C. after addition reaction mixture stirred at room temperature for 12 h. The progress of reaction was checked by TLC using mobile phase 50% ethyl acetate in pet ether. The reaction mixture was evaporated on a rotatory evaporator under reduced pressure to afford the semisolid brown compound. The suspension was diluted with water and then extracted with ethyl acetate. The organic layer was washed with brine solution, dried over anhydrous Na2SO4 and solvents were evaporated on a rotatory evaporator under reduced pressure to afford 4-(3-(4-(2-((3-bromophenyl)sulfonyl)-2-methylpropanoyl)piperazine-1-carbonyl)-4-fluorobenzyl) phthalazin-1(2H)-one (40) as colorless crystals compound (1.4 g, 32%).

$^1$H-NMR δ 12.59 (s, 1H), 8.27-8.25 (dd, J=8.0 Hz & 1.2 Hz, 1H), 7.98 (t, J=8.0 Hz, 1H), 7.93-7.91 (m, 1H), 7.90-7.87 (dd, J=7.6 Hz & 1.2 Hz, 1H), J=7.6 Hz, 2H), 7.61 (t, J=8.0 Hz, 1H), 7.45 (m, 1H), 7.39-7.27 (dd, J=6.4 Hz & 2.0 Hz, 1H), 7.25 (t, J=8.8 Hz, 1H), 4.34 (s, 2H), 3.69 (br s, 4H), 3.60 (br s, 2H), 3.29 (d, 2H), 1.59 (s, 6H)

Example 41

4-(4-fluoro-3-(4-(2-((2-fluorophenyl)thio)-2-methylpropanoyl)piperazine-1-carbonyl)benzyl)phthalazin-1(2H)-one $^1$H-NMR δ 12.59 (s, 1H), 8.26 (d, J=8.0 Hz, 1H), 7.97 (d, J=8.0 Hz, 1H), 7.89 (t, J=7.2 Hz, 1H), 7.82 (t, J=7.6 Hz, 1H), 7.51-7.45 (m, 3H), 7.39 (d, J=6.0 Hz, 1H), 7.29 (t, J=8.4 Hz, 1H), 7.22 (t, J=9.6 Hz, 2H), 4.34 (s, 2H), 3.80 (br s, 2H), 3.69 (br s, 4H), 3.29 (d, 2H), 1.43 (s, 6H)

Example 42

4-(3-(4-(2-((3-bromophenyl)thio)-2-methylpropanoyl)piperazine-1-carbonyl)-4-fluorobenzyl)phthalazin-1(2H)-one $^1$H-NMR δ 12.58 (s, 1H), 8.26 (d, J=6.8 Hz, 1H), 7.96 (d, J=8.4 Hz, 1H), 7.88 (t, J=7.2 Hz, 1H), 7.84 (t, J=8.0 Hz, 1H), 7.59 (d, J=7.6 Hz, 1H), 7.54 (d, J=1.6 Hz, 1H), 7.44 (m, 1H), 7.39-7.37 (dd, J=6.4 Hz & 1.6 Hz, 2H), 7.33 (t, J=7.6 Hz, 1H), 7.24 (t, J=9.2 Hz, 1H), 4.33 (s, 2H), 3.80 (br s, 2H), 3.67 (br s, 4H), 3.24 (d, 2H), 1.45 (s, 6H)

Example 43

4-(3-(4-(2-((3-chlorophenyl)thio)-2-methylpropanoyl)piperazine-1-carbonyl)-4-fluorobenzyl)phthalazin-1(2H)-one $^1$H-NMR δ 12.58 (s, 1H), 8.27-8.24 (dd, J=7.6 Hz & 1.2 Hz, 1H), 7.96 (d, J=8.0 Hz, 1H), 7.91-7.86 (t, J=7.2 Hz, 1H), 7.82 (t, J=8.0 Hz, 1H), 7.48-7.32 (m, 5H), 7.35-7.32 (m, 1H), 7.24 (t, J=9.2 Hz, 1H), 4.33 (s, 2H), 3.82 (br s, 21-1), 3.66 (br s, 4H), 3.26 (d, 2H), 1.45 (s, 6H)

Example 44

6-bromo-4-(4-fluoro-3-(4-(2-methyl-2-(pyridin-2-ylthio)propanoyl)piperazine-1-carbonyl)benzyl)phthalazin-1(2H)-one $^1$H-NMR δ 12.68 (s, 1H), 8.40-8.38 (m, 1H), 8.15 (d, J=8.4 Hz, 1H), 8.10 (d, J=1.6 Hz, 1H), 7.98 (dd, J=8.8 Hz and 2 Hz, 1H), 7.70-7.66 (m, 1H), 7.40-7.33 (m, 2H), 2.27 (d, J=8 Hz, 1H), 2.22 (d, J=9.2 Hz, 1H), 7.19-7.16 (m, 1H), 4.31 (s, 2H), 3.65 (m, 4H), 3.5 (s, 26H), 3.07 (s, 2H), 1.57 (s, 6H)

Example 45

4-(4-fluoro-3-(4-(2-methyl-2-((2-nitropyridin-3-yl)oxy)propanoyl)piperazine-1-carbonyl)benzyl)phthalazin-1(2H)-one $^1$H-NMR δ 12.56 (s, 1H), 8.24 (d, J=7.2 Hz, 1H), 8.18 (dd, J=4.8 & 1.2 Hz, 1H), 7.91 (brs, 1H), 7.82-7.83 (brd, 1H), 7.73 (dd, J=8.8 & 4.8 Hz, 1H), 7.48 (dd, J=8.8 & 0.8 Hz, 1H), 7.40-7.41 (brd, 1H), 7.31 (brs, 1H), 7.20 (t, J=9 Hz, 1H), 4.29 (s, 2H), 3.56-3.62 (brd, 6H), 3.10 (s, 2H), 1.59 (s, 6H)

Example 46

4-(4-fluoro-3-(4-(2-methyl-2-(phenylthio)propanoyl)piperazine-1-carbonyl)benzyl)phthalazin-1(2H)-one $^1$H-NMR δ 12.58 (s, 1H), 8.24 (t, J=4.4 Hz, 1H), 7.95 (d, J=8.0 Hz, 1H), 7.87 (dd, J=8.0 & 1.2 Hz, 1H), 7.81 (t, J=7.6 Hz, 1H), 7.40-7.45 (m, 1H), 7.33-7.38 (m, 6H), 7.23 (t, J=9 Hz, 1H), 4.32 (s, 2H), 3.67-3.82 (m, 4H), 3.24 (brs, 2H), 1.42 (s, 6H)

Example 47

4-(3-(4-(2-((4-bromophenyl)thio)-2-methylpropanoyl)piperazine-1-carbonyl)-4-fluorobenzyl)phthalazin-1(2H)-one $^1$H-NMR δ 12.59 (s, 1H), 8.26 (dd, J=8 & 1.2 Hz, 1H), 7.96 (d, J=7.6 Hz, 1H), 7.87-7.91 (m, 1H), 7.84 (t, J=4 Hz, 1H), 7.56-7.58 (m, 2H), 7.43-7.45 (m, 1H), 7.38 (dd, J=6.4 & 2 Hz, 1H), 7.31-7.33 (m, 2H), 7.25 (t, J=9 Hz, 1H), 4.34 (s, 2H), 3.60-3.80 (m, 6H), 3.24 (brs, 2H), 1.43 (s, 6H)

Example 48

4-(4-fluoro-3-(4-(2-methyl-2-(2,3,5,6-tetrafluorophenoxy)propanoyl)piperazine-1-carbonyl)benzyl)phthalazin-1(2H)-one $^1$H-NMR δ 12.59 (s, 1H), 8.24 (d, J=7.2 Hz, 1H), 7.96 (d, J=8.0 Hz, 1H), 7.87-7.74 (m, 3H), 7.45-7.37 (m, 2H), 7.23 (t, J=8.8 Hz, 1H), 4.32 (s, 2H), 3.9 (br s, 1H), 3.82 (br s, 1H), 3.61 (d, 4H), 3.22 (br s, 2H), 1.49 (s, 6H)

Example 49

4-(3-(4-(2-((2,5-dimethylphenyl)thio)-2-methylpropanoyl)piperazine-1-carbonyl)-4-fluorobenzyl)phthalazin-1(2H)-one $^1$H-NMR δ 12.60 (s, 1H), 8.26 (d, J=7.6 Hz, 1H), 7.97 (d, J=8.0 Hz, 1H), 7.91-7.86 (td, J=7.6 Hz & 1.6 Hz, 1H), 7.82 (t, J=8.0 Hz, 1H), 7.46-7.43 (m, 1H), 7.39-7.37 (dd, J=6.4 Hz & 2.0 Hz, 1H), 7.24 (d, J=9.2 Hz, 1H), 7.17 (d, J=8.0 Hz, 1H), 7.11 (s, 1H), 7.07 (d, J=8.0 Hz, 1H), 4.33 (s, 2H), 3.82 (br s, 2H), 3.66 (br s, 4H), 3.27 (d, 2H), 2.30 (s, 3H), 2.21 (s, 3H), 1.41 (s, 6H)

Example 50

4-(3-(4-(2-((2,4-dimethylphenyl)thio)-2-methylpropanoyl)piperazine-1-carbonyl)-4-fluorobenzyl)phthalazin-1(2H)-one $^1$H-NMR δ 12.60 (s, 1H), 8.26 (d, J=6.8 Hz, 1H), 7.97 (d, J=8.0 Hz, 1H), 7.91-7.87 (d, J=8.4 Hz & 1.2 Hz, 1H), 7.82 (t, J=6.8 Hz, 1H), 7.46-7.42 (m, 1H), 7.40-7.37 (dd, J=6.4 Hz & 2.4 Hz, 1H), 7.24 (d, J=9.2 Hz, 1H), 7.79 (d, J=7.6 Hz, 1H), 7.12 (br s, 1H), 6.98 (d, J=7.6 Hz, 1H), 4.33 (s, 2H), 3.81 (br s, 214), 3.67-3.58 (m, 4H), 3.27 (d, 2H), 2.33 (s, 3H), 2.26 (s, 3H), 1.98 (s, 6H)

Biological Activity—In Vitro Study

In Vitro Study

Potentiation of cell killing activity of Methyl Methane Sulphonate (MMS) by selected compounds according to present invention was evaluated in MCF-7 cell line obtained from National Centre for Cell Science, Pune, by using MTT assay according to general protocol described in *Methods in Molecular Biology*, Volume-43, *In vitro Toxicity Testing Protocol*, Chapter-6, page: 137-149. Compounds were tested for PARP 1 activity based on percent cell survival of MCF-7 cells with alkylating agent MMS. The results are summarized in Table 1.

The compounds were tested for PARP-1 inhibitory activity by using HT universal colorimetric PARP assay kit obtained from Trevigen, following manufacturer's protocol.

The results of the compounds are provided in Table 1. Result of Table 1 shows that many of the compounds are found to posses PARP 1 inhibitory activity, thus have potential to be developed as compounds for therapeutic use.

TABLE 1

PARP-1 and Cellular Potencies cell survival assay as a single therapy in MCF 7 cell

| Sr. No. | Survival affected by drug [(–MMS/+MMS)] at 100 nM | PARP-1 activity in vitro IC50 nM) |
|---|---|---|
| AZD | 2.19 | 8.0 |
| 03 | 2.07 | 11 |
| 17 | 1.93 | 13.88 |
| 19 | 2.19 | 12.37 |
| 20 | 2.15 | 14.31 |
| 21 | 1.62 | 11.97 |
| 22 | 2.1 | 5.3 |
| 23 | 2.11 | 4.23 |
| 24 | 2.28 | 4.66 |
| 25 | 2.15 | 5.94 |
| 26 | 2.59 | 6.43 |
| 27 | 2.49 | 5.17 |
| 28 | 2.08 | 7.08 |
| 29 | 2.22 | 8.6 |
| 30 | 2.22 | 9.38 |
| 31 | 1.94 | 3.05 |
| 32 | 2.08 | 5.7 |
| 33 | 1.98 | 7.9 |
| 34 | 2.85 | 6.68 |
| 35 | 3.33 | 3.56 |
| 36 | 2.59 | 5.17 |
| 37 | 1.61 | 16.49 |
| 38 | 1.96 | 5.0 |
| 39 | 2.29 | 9.47 |
| 46 | 2.28 | 10.64 |
| 47 | 2.12 | 9.16 |

I claim:

1. A compound of formula (I)

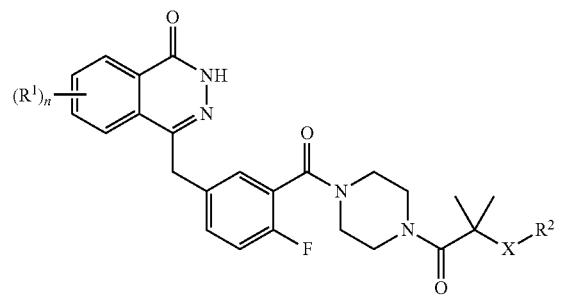

or a pharmaceutically acceptable salt, tautomer or stereoisomer thereof:

wherein, $R^1$ is independently selected from hydrogen, halo, nitro, cyano, or an unsubstituted or substituted group selected from ($C_1$-$C_{12}$)alkyl, haloalkyl, cycloalkyl, alkylthio or $OS(O)_2$alkyl, where substituents are selected from a member of the group consisting of hydroxy, oxo, halo, thio, nitro, amino, alkyl, alkoxy, haloalkyl and haloalkoxy;

n is 1, 2 or 3;

X is selected from —O—, —S—, —S(O)$_2$—, —SO—, or —NH—; and $R^2$ is an unsubstituted or substituted group selected from aryl, heteroaryl or heterocyclyl, where (i) substituents on the aryl group are selected from a member of the group consisting of halo, alkyl, alkoxy, hydroxy, haloalkyl, haloalkoxy, cyano, thioalkyl and cycloalkyl, and (ii) substituents on the heteroaryl group or heterocyclyl group are selected from a member of the group consisting of halo, alkyl, alkoxy, hydroxy, haloalkyl, haloalkoxy, aryl, aralkyl, cyano, alkylthio and thioalkyl.

2. The compound as defined in claim 1, wherein the aryl group is selected from phenyl, naphthyl, tetrahydronaphthyl, indenyl, dihydroindenyl or biphenyl.

3. The compound as defined in claim 2, wherein substituents on the aryl group are selected from halo, alkyl, alkoxy, hydroxy, haloalkyl, haloalkoxy, cyano, thioalkyl or cycloalkyl.

4. The compound as defined in in claim 1, wherein the heteroaryl group is selected from pyridyl, thienyl, furyl, pyrrolyl, indolinyl, indolyl, pyridofuranyl, pyridothienyl, thienopyrimidyl, quinolinyl, pyrimidinyl, pyrazolyl, quinazolinyl, pyridazinyl, or purinyl.

5. The compound as defined in claim 4, wherein substituents on the heteroaryl group are selected from halo, alkyl, alkoxy, hydroxy, haloalkyl, haloalkoxy, aryl, aralkyl, cyano, alkylthio or thioalkyl.

6. The compound as defined in claim 1, wherein the heterocyclyl group is selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothienyl, dihydropyranyl, dihydrofuranyl, dihydrothiazolyl, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, or thienopiperidinyl.

7. The compound as defined in claim 6, wherein substituents on the heterocyclyl group are selected from halo, alkyl, alkoxy, hydroxy, haloalkyl, haloalkoxy, aryl, aralkyl, cyano, alkylthio or thioalkyl.

8. The compound as defined in claim 1, wherein $R^1$ is substituted by a member of the group consisting of hydroxy, oxo, halo, thio, nitro, amino, alkyl, alkoxy, haloalkyl and haloalkoxy.

9. The compound as defined in claim 1, wherein $R^2$ is substituted by a member of the group consisting of halo, alkyl, alkoxy, hydroxy, haloalkyl and haloalkoxy.

10. A pharmaceutical composition comprising a therapeutically effective amount of the compound of formula (I) as defined in claim 1 and one or more pharmaceutically acceptable carriers, diluents or excipients.

11. A method for inhibiting poly(adenosine diphosphate-ribose) polymerase 1 in a subject in need thereof, comprising
    administering to the subject in need thereof a therapeutically effective amount of the compound of formula (I) as defined in claim 1 or a pharmaceutical composition thereof as defined in claim 10.

12. A compound selected from a member of the group consisting of:
    4-(4-fluoro-3-(4-(2-methyl-2-(5-(trifluoromethyl)pyridin-2-yl)oxy) propanoyl)piperazine-1-carbonyl)benzyl) phthalazin-1(2H)-one;
    4-(4-fluoro-3-(4-(2-methyl-2-(4-nitrophenoxy)propanoyl)piperazine-1-carbonyl)benzyl)phthalazin-1(2H)-one;
    4-(4-fluoro-3-(4-(2-methyl-2-(4-methoxyphenoxy)propanoyl)piperazine-1-carbonyl)benzyl)phthalazin-1(2H)-one;
    4-(4-fluoro-3-(4-(2-methyl-2-(4-chlorophenoxy)propanoyl)piperazine-1-carbonyl)benzyl) phthalazin-1(2H)-one;
    4-(4-fluoro-3-(4-(2-methyl-2-(4-fluorophenoxy)propanoyl)piperazine-1-carbonyl)benzyl) phthalazin-1(2H)-one;
    4-(4-fluoro-3-(4-(2-methyl-2-phenoxypropanoyl)piperazine-1-carbonyl)benzyl)phthalazin-1(2H)-one;
    4-(3-(4-(2-((4-chlorophenyl)thio)-2-methylpropanoyl) piperazine-1-carbonyl)-4-fluoro benzyl)phthalazin-1(2H)-one;
    4-(4-fluoro-3-(4-(2-methyl-2-(p-tolyloxy)propanoyl)piperazine-1-carbonyl)benzyl) phthalazin-1(2H)-one;
    4-(4-fluoro-3-(4-(2-(3-methoxyphenoxy)-2-methylpropanoyl)piperazine-1-carbonyl)benzyl)phthalazin-1(2H)-one;
    4-(4-fluoro-3-(4-(2-methyl-2 (naphthalen-2-yloxy)propanoyl)piperazine-1-carbonyl)benzyl)phthalazin-1(2H)-one;
    4-(3-(4-(2-((2-chlorophenyl)thio)-2-methylpropanoyl) piperazine-1-carbonyl)-4-fluoro benzyl)phthalazin-1(2H)-one;
    4-(3-(4-(2-((4-chloronaphthalen-1-yl)oxy)-2-methylpropanoyl)piperazine-1-carbonyl)-4-fluorobenzyl)phthalazin-1(2H)-one;
    4-(4-fluoro-3-(4-(2-((2-fluorophenyl)amino)propanoyl) piperazine-1-carbonyl)benzyl)phthalazin-1(2H)-one;
    4-(4-fluoro-3-(4-(2-(isoquinolin-5-yloxy)-2-methyl-propanoyl)piperazine-1-carbonyl)benzyl)phthalazin-1(2H)-one;
    4-(3-(4-(2-(2,5-dimethylphenoxy)-2-methylpropanoyl) piperazine-1-carbonyl)-4-fluoro benzyl)phthalazin-1(2H)-one;
    4-(3-(4-(2-(2,3-dichlorophenoxy)-2-methylpropanoyl) piperazine-1-carbonyl)-4-fluoro benzyl)phthalazin-1(2H)-one;
    4-(4-fluoro-3-(4-(2-methyl-2-(pyridin-2-yloxy) propanoyl)piperazine-1-carbonyl)benzyl)phthalazin-1(2H)-one;
    6-bromo-4-(3-(4-(2-(cyclopentylthio)-2-methylpropanoyl)piperazine-1-carbonyl)-4-fluoro benzyl)phthalazin-1(2H)—)-one;
    4-(4-fluoro-3-(4-(2-methyl-2-(2-nitrophenoxy)propanoyl)piperazine-1-carbonyl)benzyl)phthalazin-1(2H)-one;
    4-(3-(4-(2-(4-bromo-2-chlorophenoxy)-2-methylpropanoyl)piperazine-1-carbonyl)-4-fluorobenzyl)phthalazin-1(2H)-one;
    4-(4-fluoro-3-(4-(2-methyl-2-(3-(trifluoromethyl)phenoxy)propanoyl)piperazine-1-carbonyl)benzyl)phthalazin-1(2H)-one;
    4-(4-fluoro-3-(4-(2-((4-fluorophenyl)thio)-2-methylpropanoyl)piperazine-1-carbonyl)benzyl)phthalazin-1(2H)-one;
    4-(4-fluoro-3-(4-(2-methyl-2-(phenylsulfonyl)propanoyl) piperazine-1-carbonyl)benzyl) phthalazin-1(2H)-one;
    4-(4-fluoro-3-(4-(2-((4-fluorophenyl)sulfonyl)-2-methylpropanoyl)piperazine-1-carbonyl)benzyl)phthalazin-1(2H)-one;
    4-(4-fluoro-3-(4-(2-((4-fluorophenyl)sulfinyl)-2-methylpropanoyl)piperazine-1-carbonyl)benzyl)phthalazin-1(2H)-one;
    4-(3-(4-(2-(2,4-difluorophenoxy)-2-methylpropanoyl) piperazine-1-carbonyl)-4-fluoro benzyl)phthalazin-1(2H)-one;
    4-(3-(4-(2-((2,4-difluorophenyl)thio)-2-methylpropanoyl)piperazine-1-carbonyl)-4-fluoro benzyl)phthalazin-1(2H)-one;
    4-(4-fluoro-3-(4-(2-((3-methoxyphenyl)thio)-2-methylpropanoyl)piperazine-1-carbonyl)benzyl)phthalazin-1(2H)-one;
    4-(3-(4-(2-((2-bromophenyl)thio)-2-methylpropanoyl) piperazine-1-carbonyl)-4-fluoro benzyl)phthalazin-1(2H)-one;
    4-(3-(4-(2-((3,4-dichlorophenyl)thio)-2-methylpropanoyl)piperazine-1-carbonyl)-4-fluoro benzyl)phthalazin-1(2H)-one;
    4-(3-(4-(2-((2,4-dichlorophenyl)thio)-2-methylpropanoyl)piperazine-1-carbonyl)-4-fluoro benzyl)phthalazin-1(2H)-one;

4-(4-fluoro-3-(4-(2-((3-fluorophenyl)thio)-2-methylpropanoyl)piperazine-1-carbonyl)benzyl)phthalazin-1(2H)-one;

4-(3-(4-(2-((2,5-dichlorophenyl)thio)-2-methylpropanoyl)piperazine-1-carbonyl)-4-fluoro benzyl)phthalazin-1(2H)-one;

4-(4-fluoro-3-(4-(2-((4-fluorophenyl)amino)-2-methylpropanoyl)piperazine-1-carbonyl-benzyl)phthalazin-1(2H)-one;

4-(4-fluoro-3-(4-(2-methyl-2-(phenylamino)-propanoyl)piperazine-1-carbonyl)benzyl) phthalazin-1(2H)-one;

4-(3-(4-(2-(cyclopentylthio)-2-methylpropanoyl)piperazine-1-carbonyl)-4-fluorobenzyl) phthalazin-1(2H)-one;

4-(3-(4-(2-(4-bromo-3,5-dimethylphenoxy)-2-methylpropanoyl)piperazine-1-carbonyl)-4-fluorobenzyl)phthalazin-1(2H)-one;

4-(4-fluoro-3-(4-(2-methyl-2-(pyridin-2-ylthio)propanoyl)piperazine-1-carbonyl)benzyl) phthalazin-1(2H)-one;

4-(3-(4-(2-(2,4-dichlorophenylsulfinyl)-2-methylpropanoyl)piperazine-1-carbonyl)-4-fluorobenzyl)phthalazin-1(2H)-one;

4-(3-(4-(2-((3-bromophenyl)sulfonyl)-2-methylpropanoyl)piperazine-1-carbonyl)-4-fluoro benzyl)phthalazin-1(2H)-one;

4-(4-fluoro-3-(4-(2-((2-fluorophenyl)thio)-2-methylpropanoyl)piperazine-1-carbonyl)benzyl)phthalazin-1(2H)-one;

4-(3-(4-(2-((3-bromophenyl)thio)-2-methylpropanoyl)piperazine-1-carbonyl)-4-fluoro benzyl)phthalazin-1(2H)-one;

4-(3-(4-(2-((3-chlorophenyl)thio)-2-methylpropanoyl)piperazine-1-carbonyl)-4-fluoro benzyl)phthalazin-1(2H)-one;

6-bromo-4-(4-fluoro-3-(4-(2-methyl-2-(pyridin-2-ylthio)propanoyl)piperazine-1-carbonyl)benzyl)phthalazin-1(2H)-one;

4-(4-fluoro-3-(4-(2-methyl-2-((2-nitropyridin-3-yl)oxy)propanoyl)piperazine-1-carbonyl)benzyl)phthalazin-1(2H)-one;

4-(4-fluoro-3-(4-(2-methyl-2-(phenylthio)propanoyl)piperazine-1-carbonyl)benzyl) phthalazin-1(2H)-one;

4-(3-(4-(2-((4-bromophenyl)thio)-2-methylpropanoyl)piperazine-1-carbonyl)-4-fluoro benzyl)phthalazin-1(2H)-one;

4-(4-fluoro-3-(4-(2-methyl-2-(2,3,5,6-tetrafluorophenoxy)propanoyl)piperazine-1-carbonyl)benzyl)phthalazin-1(2H)-one;

4-(3-(4-(2-((2,5-dimethylphenyl)thio)-2-methylpropanoyl)piperazine-1-carbonyl)-4-fluoro benzyl)phthalazin-1(2H)-one; and 4-(3-(4-(2-((2,4-dimethylphenyl)thio)-2-methylpropanoyl)piperazine-1-carbonyl)-4-fluoro benzyl)phthalazin-1(2H)-one;

or a pharmaceutically acceptable salt, tautomer or stereoisomer thereof.

\* \* \* \* \*